US012728136B2

(12) United States Patent
Zhou et al.

(10) Patent No.: US 12,728,136 B2
(45) Date of Patent: Sep. 8, 2026

(54) LIPOSOMAL NANO FORMULATION OF COMBINATIONAL ANTIBIOTICS AND THE USES THEREOF

(71) Applicant: Purdue Research Foundation, West Lafayette, IN (US)

(72) Inventors: Qi Zhou, West Lafayette, IN (US); Shaoning Wang, BenXi (CN)

(73) Assignee: Purdue Research Foundation, West Lafayette, IN (US)

( * ) Notice: Subject to any disclaimer, the term of this patent is extended or adjusted under 35 U.S.C. 154(b) by 7 days.

(21) Appl. No.: 17/051,791

(22) PCT Filed: Apr. 30, 2019

(86) PCT No.: PCT/US2019/029945
§ 371 (c)(1),
(2) Date: Oct. 30, 2020

(87) PCT Pub. No.: WO2019/213101
PCT Pub. Date: Nov. 7, 2019

(65) Prior Publication Data

US 2021/0113595 A1 Apr. 22, 2021

Related U.S. Application Data

(60) Provisional application No. 62/664,440, filed on Apr. 30, 2018.

(51) Int. Cl.

| | |
|---|---|
| ***A61K 31/685*** | (2006.01) |
| ***A61K 9/127*** | (2025.01) |
| ***A61K 31/4709*** | (2006.01) |
| ***A61K 38/12*** | (2006.01) |

(52) U.S. Cl.
CPC ............ *A61K 31/685* (2013.01); *A61K 9/127* (2013.01); *A61K 31/4709* (2013.01); *A61K 38/12* (2013.01)

(58) Field of Classification Search
CPC .. A61K 31/685; A61K 9/127; A61K 31/4709; A61K 38/12; A61K 9/1277; A61K 47/183; A61K 47/34; A61K 9/0075; A61K 9/1272; A61K 9/19; A61K 31/496; A61K 47/26; A61K 47/32; C07K 7/62; A61P 31/00
See application file for complete search history.

(56) References Cited

U.S. PATENT DOCUMENTS

| | | | | |
|---|---|---|---|---|
| 5,316,771 | A * | 5/1994 | Barenholz ............ | A61K 9/1278 264/4.1 |
| 2003/0113369 | A1 * | 6/2003 | Martin ................. | A61K 9/1271 424/450 |
| 2006/0280691 | A1 | 12/2006 | Wang | |
| 2007/0042030 | A1 | 2/2007 | Cevc | |
| 2007/0077290 | A1 * | 4/2007 | Li .......................... | A61K 9/127 514/35 |
| 2010/0028334 | A1 * | 2/2010 | Cottarel ................. | A61K 31/16 514/3.3 |
| 2015/0004219 | A1 * | 1/2015 | Barenholz ............ | A61K 9/1278 514/283 |
| 2015/0283133 | A1 | 10/2015 | Gonda et al. | |
| 2016/0101124 | A1 * | 4/2016 | Halwani ............ | A61K 31/7036 424/450 |

FOREIGN PATENT DOCUMENTS

| | | | |
|---|---|---|---|
| CA | 2983504 | * | 6/2014 |
| WO | 2010/056927 | * | 5/2010 |

OTHER PUBLICATIONS

Arshinova, O.Y., Sanarova, E.V., Lantsova, A.V et al. Lyophilization of liposomal drug forms (Review). Pharm Chem J 46, 228-233 (2012). https://doi.org/10.1007/s11094-012-0768-2 (Year: 2012).*
Kubesch, P et al. "Interaction of polymyxin B nonapeptide with anionic phospholipids." Biochemistry vol. 26,8 (1987): 2139-49. doi: 10.1021/bi00382a012 (Year: 1987).*
Zhou, et al., The AAPS Journal, 2013, 16(1), 37-47.

(Continued)

*Primary Examiner* — Sahana S Kaup
*Assistant Examiner* — Toriana N. Vigil
(74) *Attorney, Agent, or Firm* — Purdue Research Foundation

(57) ABSTRACT

The present disclosure generally relates to a process for manufacturing liposomes containing polymyxin and quinolone as a treatment for bacterial infections. In particular, the present invention utilizes an anionic lipid as an essential component of a liposome for efficient encapsulation of polymyxin and quinolone, which affords a stable more efficient pharmaceutical composition for the treatment of a bacterial infection, especially infections of the lungs. Pharmaceutical compositions and methods of treatment are within the scope of this invention.

FIG. 1A

10 Claims, 11 Drawing Sheets

(56) References Cited

OTHER PUBLICATIONS

Tran, et al., Int J Antimicrob Agents. Dec. 2016 ; 48(6): 592-597.
Shetty, et al., Pharm. Res. 2018,35:7.
Mangal, et al., European J. Pharmaceutics and Biopharmacetics, 2015, 94, 160-169.
Buyck, et al, Antimicrobial Agents and Chemotherapy, 2015, 59, 258-268.
Mangal, et al., Pharmaceutical Research, 2018, 35:28.
Lavorini, et al., Multidisciplinary Respiratory Medicine, 2017, 12:11.
Park, et al., Int'l J. Pharmaceutics, 2013, 455, 374-392.
68025-02_PCT_ISR-WO.

* cited by examiner

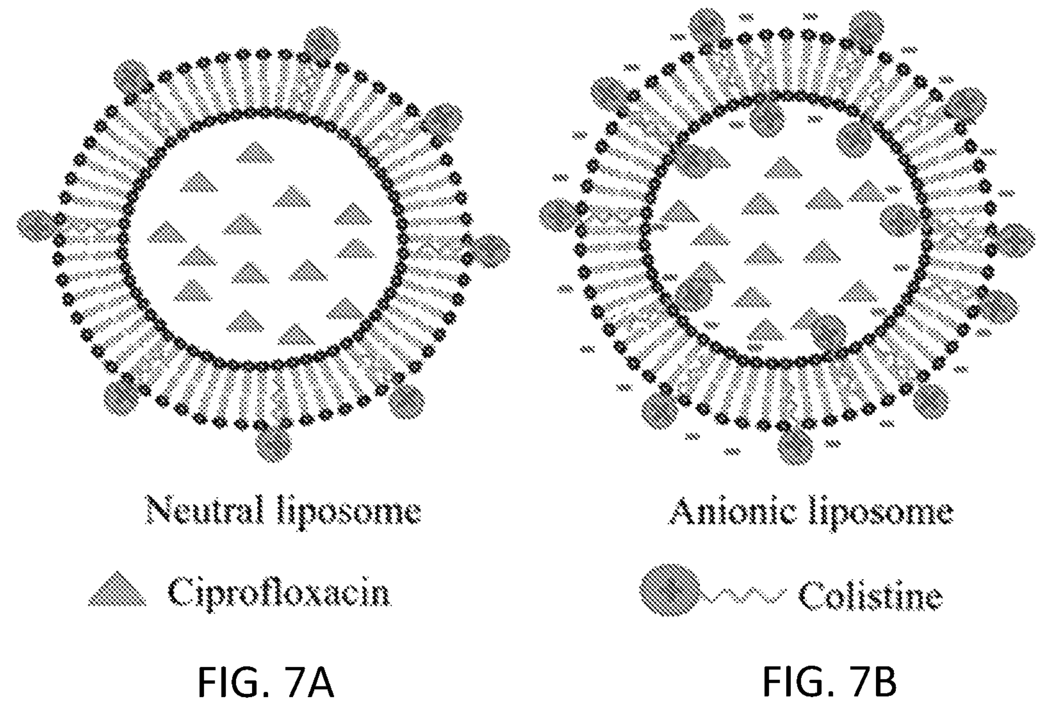
FIG. 7A
FIG. 7B
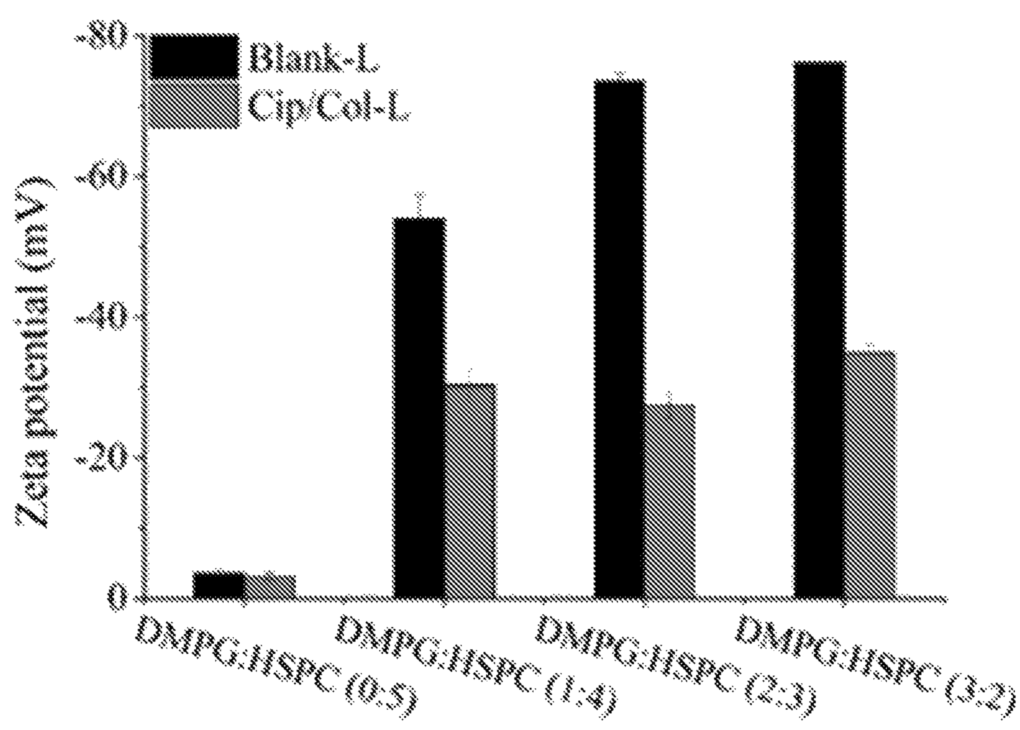
FIG. 8

LIPOSOMAL NANO FORMULATION OF COMBINATIONAL ANTIBIOTICS AND THE USES THEREOF

CROSS REFERENCE TO RELATED APPLICATIONS

This present patent application is a national stage entry under 35 U.S.C. § 371(b) of International Application No. PCT/US19/29945, filed on Apr. 30, 2019, which relates to and claims the priority benefit of U.S. Provisional Application Ser. No. 62/664,440, filed Apr. 30, 2018, the content of which is hereby incorporated herein by reference in its entirety.

GOVERNMENT SUPPORT CLAUSE

This invention was made with government support under AI132681 awarded by the National Institutes of Health. The government has certain rights in the invention.

TECHNICAL FIELD

The present application relates generally to a process for manufacturing uniform sized liposomes containing polymyxin and quinolone as a treatment for bacterial infections. In particular, the present invention utilizes an anionic lipid as an essential component of a liposome for efficient encapsulation of polymyxin and quinolone, which affords a stable more efficient pharmaceutical composition for the treatment of a bacterial infection.

BACKGROUND

This section introduces aspects that may help facilitate a better understanding of the disclosure. Accordingly, these statements are to be read in this light and are not to be understood as admissions about what is or is not prior art.

Multidrug-resistance (MDR) in Gram-negative bacteria, such as *Pseudomonas aeruginosa* had become a serious challenge for physicians in the treatment of respiratory infections, accounting for approximately 20% of ventilator-associated pneumonias (VAP) with mortality rates reaching up to 50% (Stefani S, et al., *Int. J. Med. Microbiol.* 2017, 307:353-362; Trinh T D, et al., *Diagn Micro. Infec. Dis.* 2017, 89: 61-66)). Limited therapeutic options against these MDR Gram-negative 'superbugs' have driven the revival of colistin (Col, also known as polymyxin E) as the last line of defense (Li J. et al., *Lancet Infect Dis.* 2006, 6:589-601). Unfortunately, because of the rapid increase in clinical use over the last decade, colistin does not escape from resistance development (Bergen P J, et al., *Antimicrob Agents Ch.* 2010, 54:3783-3789; Johansen H K, et al., *J Cyst Fibros.* 2008, 7:391-397). In addition, dose-dependent nephrotoxicity limited the use of high dose of colistin monotherapy (Ordooei J A, et al., *Eur J Clin Pharmacol* 2015, 71:801-810). Colistin based combination therapies may offer viable alternative treatment options with synergistic antimicrobial activities or minimized antimicrobial resistance such as rifampicin, azithromicin, meropenem, doripenem and ciprofloxacin (Petrosillo N. et al., *Clin Microbiol Infec.* 2008, 14:816-827). Particularly, the combination therapy of nebulized colistin (Col) and oral ciprofloxacin (Cip) has been proved to successfully eradicate *P. aeruginosa* from the respiratory tract of CF patients without development of antibiotic resistance nor serious adverse effects for 15 years in the Danish Cystic Fibrosis Center and a few other centers.

For the combination therapy of Col and Cip, delivery of both drugs simultaneously and directly to the infection sites in the lungs could be a promising approach for the treatment of MDR Gram-negative lower respiratory tract infections (or lung infections). The capability to encapsulate both lipophilic and hydrophilic compounds makes liposomes a favorable nanoparticle carrier for co-deliver combinational drugs (Zununi V S, et al., *Mater Sci Eng C Mater Biol Appl.* 2017, 71:1327-1341).

For the pulmonary drug delivery, liposomal formulations have distinctive advantages such as prolonged release of the drug and thus a longer action at the site of infections, reduction in frequency of administrations with improved patient compliance, and minimize the local irritations associated with the drug. Furthermore, liposomal particles with a nano-meter size may escape from macrophage clearance and therefore enable longer drug retention in the deep lungs. As an amphipathic weak base (FIG. 1A), Cip can be encapsulated in liposomes through the remote-loading method (Gubernator J, *Expert Opin Drug Deliv.* 2011, 8:565-580). Nebulized liposomal formulations of ciprofloxacin were shown to be efficacious with superior tolerability in Cystic Fibrosis (CF) and non-CF bronchitis patients (D J Serisier, et al., *Thorax,* 2013, 68, 812-817; P Bruinenberg, et al., *Respiratory Drug Delivery,* 2010, pp. 73-82). Col also has an amphipathic structure, with five positively charged amine residues and a hydrophobic acyl chain (FIG. 1B). The encapsulation efficiency of Col in the neutral liposomes (NL) is usually low (Omri A, et al., *Biochem Pharmcol* 2002, 64:1407-1413). Li et al. found through the electrostatic interaction with anionic lipid, Col can be effectively loaded in liposomes (Li Y, et al., *Int J Pharm.* 2016, 515:20-29). Effective co-formulation of Col and Cip remains to be a challenge and there are unmet needs in clinical applications of those compounds.

SUMMARY

The present disclosure generally relates to a process for manufacturing uniform sized liposomes containing Col and Cip as a treatment for bacterial infections. In particular, the present invention utilizes an anionic lipid as an essential component of a liposome for efficient encapsulation of Cip and Col, which affords a stable more efficient pharmaceutical composition for the treatment of a bacterial infection, especially infections of the lungs. Pharmaceutical compositions and methods of treatment are within the scope of this invention.

In some illustrative embodiments, this present invention relates to a pharmaceutical composition comprising polymyxin, quinolone, a phosphatidylcholine (PC), an anionic lipid and cholesterol, wherein polymyxin and quinolone are encapsulated into a liposome formed by said PC, anionic lipid and cholesterol.

In some illustrative embodiments, this present invention relates to a pharmaceutical composition disclosed herein, wherein said polymyxin is colistin or polymyxin B or its pharmaceutically acceptable salt; a quinolone is ciprofloxacin, levofloxacin, moxifloxacin, gemifloxacin, gatifloxacin, garenoxacin or its pharmaceutically acceptable salt.

In some illustrative embodiments, this present invention relates to a pharmaceutical composition disclosed herein, wherein said phosphatidylcholine (PC) is soybean phosphatidylcholine (SPC), egg phosphatidylcholine (EPC), hydrogenated soybean phosphatidylcholine (HSPC), 1,2-Dimyristoyl-sn-glycero-3-phosphocholine (DMPC), 1,2-Dipalmitoyl-sn-glycero-3-phosphocholine (DPPC), 1,2-

Distearoyl-sn-glycero-3-phosphocholine (DSPC), or 1,2-Dioleoyl-sn-glycero-3-phosphocholine (DOPC).

In some illustrative embodiments, this present invention relates to a pharmaceutical composition disclosed herein, wherein said anionic lipid is a phosphoglycerol (PG) selected from the group consisting of 1,2-distearoyl-sn-glycero-3-phosphoglycerol (DSPG), 1,2-Dimyristoyl-sn-glycero-3-phosphoglycerol (DMPG), and 1,2-Dipalmitoyl-sn-glycero-3-phosphoglycerol (DPPG); or a phosphatidic acid (PA) selected from the group consisting of 1,2-Dimyristoyl-sn-glycero-3-phosphatidic acid (DMPA), 1,2-Dipalmitoyl-sn-glycero-3-phosphatidic acid (DPPA), and 1,2-Dimyristoyl-sn-glycero-3-phosphatidic acid (DSPA).

In some illustrative embodiments, this present invention relates to a pharmaceutical composition disclosed herein, wherein said PG is a sodium salt or an ammonium salt and said PA is a sodium salt.

In some illustrative embodiments, this present invention relates to a pharmaceutical composition disclosed herein, wherein said PC and anionic lipid are in a ratio of about 1:20 to about 20:1 (mol/mol).

In some illustrative embodiments, this present invention relates to a pharmaceutical composition disclosed herein, wherein said liposome is manufactured by an active drug loading method.

In some illustrative embodiments, this present invention relates to a pharmaceutical composition disclosed herein, wherein said liposome is manufactured by a passive drug loading method.

In some other illustrative embodiments, this present invention relates to a process for preparing a pharmaceutical composition, further comprising a step of freeze-drying of said pharmaceutical composition.

In some illustrative embodiments, this present invention relates to a process for preparing a pharmaceutical composition, further comprising a step of spray freeze-drying of said pharmaceutical composition.

In some illustrative embodiments, this present invention relates to a process for preparing a pharmaceutical composition comprising the steps of a. dissolving a phosphatidylcholine (PC), an anionic lipid and cholesterol in an organic solvent to prepare a solution;
b. evaporating said organic solvent from said solution of a PC, an anionic lipid and cholesterol to form a dry lipid film;
c. hydrating said dry lipid film with a solution of $(NH_4)_2SO_4$ about 100-500 mM at an elevated temperature to afford a suspension of multilamellar liposomes;
d. ultrasonicating said suspension of multilamellar liposomes and then extruding ultrasonicated suspension through a polycarbonate membrane of about 200 nm pore size to afford a suspension of unilamellar liposomes (LUVs);
e. passing said suspension of unilamellar liposomes (LUVs) through a cation exchange column pre-equilibrated with a sucrose aqueous solution of about 10% to remove extra liposomal of $NH_4^+$ to afford a suspension of liposomes with a gradient of $(NH_4)_2SO_4$; and
f. encapsulating a polymyxin compound and a quinolone compound, or a pharmaceutically acceptable salt thereof, respectively, into said liposomes with a gradient of $(NH_4)_2SO_4$ by incubating a solution of said polymyxin compound and said quinolone compound, or a pharmaceutically acceptable salt thereof, respectively, with said liposomes at an elevated temperature to afford a pharmaceutical composition.

In some other illustrative embodiments, this present invention relates to a process for preparing a pharmaceutical composition as disclosed herein, further comprising a step of freeze-drying of said pharmaceutical composition.

In some illustrative embodiments, this present invention relates to a process for preparing a pharmaceutical composition as disclosed herein, further comprising a step of spray freeze-drying of said pharmaceutical composition.

In some illustrative embodiments, this present invention relates to a process for preparing a pharmaceutical composition as disclosed herein, wherein said polymyxin is colistin, polymyxin B or a pharmaceutically acceptable salt thereof; and said quinolone is ciprofloxacin, levofloxacin, moxifloxacin, gemifloxacin, gatifloxacin, garenoxacin, or a pharmaceutically acceptable salt thereof.

In some illustrative embodiments, this present invention relates to a process for preparing a pharmaceutical composition as disclosed herein, wherein said polymyxin is colistin methanesulfonate; and said quinolone is ciprofloxacin, levofloxacin, moxifloxacin, gemifloxacin, gatifloxacin, garenoxacin, or a pharmaceutically acceptable salt thereof.

In some illustrative embodiments, this present invention relates to a process for preparing a pharmaceutical composition as disclosed herein, wherein said phosphatidylcholine (PC) is soybean phosphatidylcholine (SPC), egg phosphatidylcholine (EPC), hydrogenated soybean phosphatidylcholine (HSPC), 1,2-Dimyristoyl-sn-glycero-3-phosphocholine (DMPC), 1,2-Dipalmitoyl-sn-glycero-3-phosphocholine (DPPC), 1,2-Distearoyl-sn-glycero-3-phosphocholine (DSPC), or 1,2-Dioleoyl-sn-glycero-3-phosphocholine (DOPC).

In some illustrative embodiments, this present invention relates to a process for preparing a pharmaceutical composition as disclosed herein, wherein said PC and anionic lipid are in a ratio of about 1:20 to about 20:1 (mol/mol ratio).

In some illustrative embodiments, this present invention relates to a process for preparing a pharmaceutical composition as disclosed herein, wherein said anionic lipid is a phosphoglycerol (PG) selected from the group consisting of 1,2-distearoyl-sn-glycero-3-phosphoglycerol (DSPG), 1,2-Dimyristoyl-sn-glycero-3-phosphoglycerol (DMPG), and 1,2-Dipalmitoyl-sn-glycero-3-phosphoglycerol (DPPG), or a pharmaceutically acceptable salt thereof; or a phosphatidic acid (PA) selected from the group consisting of 1,2-Dimyristoyl-sn-glycero-3-phosphatidic acid (DMPA), 1,2-Dipalmitoyl-sn-glycero-3-phosphatidic acid (DPPA), and 1,2-Dimyristoyl-sn-glycero-3-phosphatidic acid (DSPA), or a pharmaceutically acceptable salt thereof.

In some illustrative embodiments, this present invention relates to a process for preparing a pharmaceutical composition as disclosed herein, wherein said PG is a salt and said PA is a salt.

In some illustrative embodiments, this present invention relates to a process for preparing a pharmaceutical composition as disclosed herein, wherein said phosphoglycerol (PG) is a sodium salt or an ammonium salt and said phosphatidic acid (PA) is a sodium salt.

In some illustrative embodiments, this present invention relates to a process for preparing a pharmaceutical composition as disclosed herein, wherein said liposome is manufactured by an active drug loading method.

In some illustrative embodiments, this present invention relates to a process for preparing a pharmaceutical composition as disclosed herein, wherein said liposome is manufactured by a passive drug loading method.

In some illustrative embodiments, this present invention relates to a process for preparing a pharmaceutical composition as disclosed herein, wherein said polymyxin and quinolone are in a ratio of from about 1:10 to about 10:1.

In some illustrative embodiments, this present invention relates to a process for preparing a pharmaceutical composition as disclosed herein, wherein said aqueous solution of polymyxin and quinolone comprises about 0.5-50 mg/mL of polymyxin and quinolone.

In some illustrative embodiments, this present invention relates to a process for preparing a pharmaceutical composition as disclosed herein, wherein said solution of polymyxin and quinolone comprises about 0.5-50 mg/mL of polymyxin and quinolone.

In some illustrative embodiments, this present invention relates to a pharmaceutical product manufactured according to the process as disclosed herein.

In some illustrative embodiments, this present invention relates to a method for treating a subject with an infection by a bacterium comprising the step of administrating a therapeutically effective amount of the pharmaceutical composition as disclosed herein.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein:

FIGS. 7A-7B illustrate the distribution of ciprofloxacin and colistin in neutral or anionic liposomes. FIG. 7A: in the neutral liposomes, few colistin was associated with the outer lipid membrane with hydrophobic acyl chain inserted in the lipid bilayer and the hydrophilic residue exposed on the outer-surface of liposomes; FIG. 7B: in the anionic liposomes, through the electrostatic attraction, more colistin was associated with the outer lipid membrane, and some penetrated in the inner membrane. Ciprofloxacin was located in the inner aqueous phase of liposomes through remote loading method regardless of neutral liposomes or anionic liposomes.

FIG. 8 shows Zeta potentials of liposomes of various DMPG/HSPC ratios (n=3, mean±SD).

DETAILED DESCRIPTION

Figures 1A, 1B, 2:
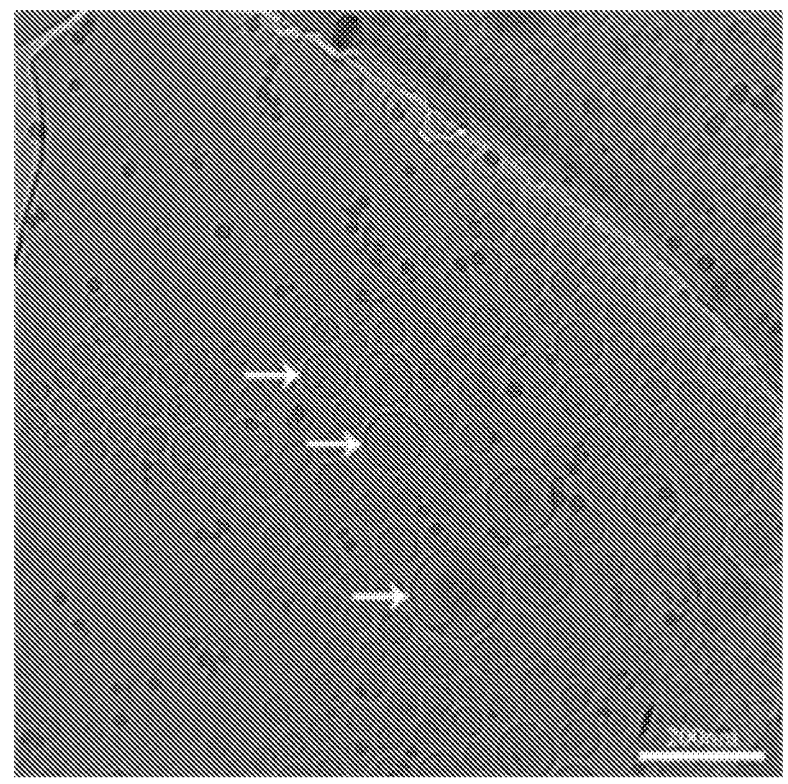
FIG. 1A shows chemical structures of ciprofloxacin.
FIG. 1B shows chemical structures of colistin.
FIG. 2 shows the cryo-TEM image of Cip/Col anionic liposomes. Scale bar represents 200 nm. Arrows indicate typical liposomes.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The present disclosure generally relates to a process for manufacturing uniform sized liposomes of about 130 nm containing polymyxin and quinolone as a treatment for bacterial infections. In particular, the present invention utilizes an anionic lipid as an essential component of a liposome for efficient encapsulation of polymyxin and quinolone, which affords a stable more efficient pharmaceutical composition for the treatment of a bacterial infection, especially infections of the lungs. Pharmaceutical compositions and methods of treatment are within the scope of this invention.

In some illustrative embodiments, this present invention relates to a pharmaceutical composition comprising colistin (Col), ciprofloxacin (Cip), a phosphatidylcholine (PC), an anionic lipid and cholesterol, wherein Col and Cip are encapsulated into a liposome formed by said PC, anionic lipid and cholesterol through a gradient of $(NH_4)_2SO_4$ method.

In some illustrative embodiments, this present invention relates to a pharmaceutical composition disclosed herein, wherein said phosphatidylcholine (PC) is soybean phosphatidylcholine (SPC), egg phosphatidylcholine (EPC), hydrogenated soybean phosphatidylcholine (HSPC), 1,2-Dimyristoyl-sn-glycero-3-phosphocholine (DMPC), 1,2-Dipalmitoyl-sn-glycero-3-phosphocholine (DPPC), 1,2-

Distearoyl-sn-glycero-3-phosphocholine (DSPC), or 1,2-Dioleoyl-sn-glycero-3-phosphocholine (DOPC).

In some illustrative embodiments, this present invention relates to a pharmaceutical composition disclosed herein, wherein said anionic lipid is a phosphoglycerol (PG) selected from the group consisting of 1,2-distearoyl-sn-glycero-3-phosphoglycerol (DSPG), 1,2-Dimyristoyl-sn-glycero-3-phosphoglycerol (DMPG), and 1,2-Dipalmitoyl-sn-glycero-3-phosphoglycerol (DPPG); or a phosphatidic acid (PA) selected from the group consisting of 1,2-Dimyristoyl-sn-glycero-3-phosphatidic acid (DMPA), 1,2-Dipalmitoyl-sn-glycero-3-phosphatidic acid (DPPA), and 1,2-Dimyristoyl-sn-glycero-3-phosphatidic acid (DSPA).

In some illustrative embodiments, this present invention relates to a process for preparing a pharmaceutical composition disclosed herein, wherein said phosphoglycerol (PG) is a sodium salt or an ammonium salt and said phosphatidic acid (PA) is a sodium salt.

In some illustrative embodiments, this present invention relates to a pharmaceutical composition disclosed herein, wherein said PC and anionic lipid are in a ratio of about 1:20 to about 20:1 (mol/mol).

In some other illustrative embodiments, this present invention relates to a pharmaceutical composition disclosed herein, wherein said liposome with a gradient of $(NH_4)_2SO_4$ is manufactured according to the steps of a. dissolving a PC, an anionic lipid and cholesterol in an organic solvent to prepare a solution;
b. evaporating said organic solvent from said solution of a PC, an anionic lipid and cholesterol to form a dry lipid film;
c. hydrating a dry lipid film with a solution of $(NH_4)_2SO_4$ about 100-500 mM at an elevated temperature to afford a suspension of multilamellar liposomes;
d. ultrasonicating said suspension of multilamellar liposomes and then extruding ultrasonicated suspension through a polycarbonate membrane of about 200 nm pore size to afford a suspension of unilamellar liposomes (LUVs); and
e. passing said a suspension of unilamellar liposomes (LUVs) through a cation exchange column pre-equilibrated with a sucrose aqueous solution of about 10% to remove extra liposomal of $NH_4^+$ to afford a suspension of liposomes with a gradient of $(NH_4)_2SO_4$.

In some illustrative embodiments, this present invention relates to a pharmaceutical composition disclosed herein, wherein Col and Cip are encapsulated into said liposome with a gradient of $(NH_4)_2SO_4$ by incubating an aqueous solution of Col and Cip with said liposomes at an elevated temperature.

In some illustrative embodiments, this present invention relates to a pharmaceutical composition disclosed herein, wherein said elevated temperature ranges from about 30° C. to about 80° C.

In some illustrative embodiments, this present invention relates to a pharmaceutical composition disclosed herein, wherein Col and Cip are in a ratio of about 1:10 to 10:1 (mol/mol).

In some illustrative embodiments, this present invention relates to a pharmaceutical composition manufactured according to the process disclosed herein, wherein said aqueous solution of Col and Cip comprises about 0.5-50 mg/mL of Col and Cip.

In some illustrative embodiments, this present invention relates to a pharmaceutical composition manufactured according to the process disclosed herein, further comprising one or more pharmaceutically acceptable excipients.

In some illustrative embodiments, this present invention relates to a process for preparing a pharmaceutical composition comprising the steps of a. dissolving a phosphatidylcholine (PC), an anionic lipid and cholesterol in an organic solvent to prepare a solution;
b. evaporating said organic solvent from said solution of a PC, an anionic lipid and cholesterol to form a dry lipid film;
c. hydrating said dry lipid film with a solution of $(NH_4)_2SO_4$ about 100-500 mM at an elevated temperature to afford a suspension of multilamellar liposomes;
d. ultrasonicating said suspension of multilamellar liposomes and then extruding ultrasonicated suspension through a polycarbonate membrane of about 200 nm pore size to afford a suspension of unilamellar liposomes (LUVs);
e. passing said a suspension of unilamellar liposomes (LUVs) through a cation exchange column pre-equilibrated with a sucrose aqueous solution of about 10% to remove extra liposomal of $NH_4^+$ to afford a suspension of liposomes with a gradient of $(NH_4)_2SO_4$; and
f. encapsulating Col and Cip into said liposomes with a gradient of $(NH_4)_2SO_4$ by incubating the mixture of an aqueous solution of Col and Cip with said liposomes at an elevated temperature to afford a pharmaceutical composition.

In some other illustrative embodiments, this present invention relates to a process for preparing a pharmaceutical composition, further comprising a step of freeze-drying of said pharmaceutical composition.

In some illustrative embodiments, this present invention relates to a process for preparing a pharmaceutical composition, further comprising a step of spray freeze-drying of said pharmaceutical composition.

In some illustrative embodiments, this present invention relates to a process for preparing a pharmaceutical composition disclosed herein, wherein said elevated temperature ranges from about 30° C. to about 80° C.

In some illustrative embodiments, this present invention relates to a process for preparing a pharmaceutical composition disclosed herein, wherein said phosphatidylcholine (PC) is soybean phosphatidylcholine (SPC), egg phosphatidylcholine (EPC), hydrogenated soybean phosphatidylcholine (HSPC), 1,2-Dimyristoyl-sn-glycero-3-phosphocholine (DMPC), 1,2-Dipalmitoyl-sn-glycero-3-phosphocholine (DPPC), 1,2-Distearoyl-sn-glycero-3-phosphocholine (DSPC), or 1,2-Dioleoyl-sn-glycero-3-phosphocholine (DOPC).

In some illustrative embodiments, this present invention relates to a process for preparing a pharmaceutical composition disclosed herein, wherein said anionic lipid is a phosphoglycerol (PG) selected from the group consisting of 1,2-distearoyl-sn-glycero-3-phosphoglycerol (DSPG), 1,2-Dimyristoyl-sn-glycero-3-phosphoglycerol (DMPG), and 1,2-Dipalmitoyl-sn-glycero-3-phosphoglycerol (DPPG); or a phosphatidic acid (PA) selected from the group consisting of 1,2-Dimyristoyl-sn-glycero-3-phosphatidic acid (DMPA), 1,2-Dipalmitoyl-sn-glycero-3-phosphatidic acid (DPPA), and 1,2-Dimyristoyl-sn-glycero-3-phosphatidic acid (DSPA).

In some illustrative embodiments, this present invention relates to a process for preparing a pharmaceutical composition disclosed herein, wherein said phosphoglycerol (PG) is a sodium salt or an ammonium salt and said phosphatidic acid (PA) is a sodium salt.

In some illustrative embodiments, this present invention relates to a process for preparing a pharmaceutical composition disclosed herein, wherein said 1,2-distearoyl-sn-glycero-3-phosphoglycerol is a sodium salt (DSPG-Na).

In some illustrative embodiments, this present invention relates to a process for preparing a pharmaceutical composition disclosed herein, wherein Col and Cip are in a ratio of about 1:10 to about 10:1.

In some illustrative embodiments, this present invention relates to a process for preparing a pharmaceutical composition disclosed herein, wherein said aqueous solution of Col and Cip comprises about 0.5-50 mg/mL of Col and for Cip.

In some illustrative embodiments, this present invention relates to a pharmaceutical product manufactured according to the process disclosed herein.

In some illustrative embodiments, this present invention relates to a method for treating a subject with an infection by a bacterium comprising the step of administrating a therapeutically effective amount of the pharmaceutical composition disclosed herein.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 20%, within 10%, within 5%, or within 1% of a stated value or of a stated limit of a range.

In the present disclosure the term "substantially" can allow for a degree of variability in a value or range, for example, within 80%, within 90%, within 95%, or within 99% of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

ABBREVIATIONS

Cipro Ciprofloxacin hydrochloride monohydrate
Col Colistin sulfate
Cipro-Col-Lips Ciprofloxacin-colistin liposomes
PDI Polydispersity index
EE Encapsulation efficiency
DPI Dry powder inhaler
USFD Ultrasonic spray freeze drying
ED Emitted dose
FPF Fine particle fraction
PXRD Powder X-ray diffraction
MSLI Multi-stage liquid impinger
SEM Scanning electron microscopy
F68 Poloxamer 188
F127 Poloxamer 407
PVP 10 Polyvinylpyrrolidone 10
PVP K30 Polyvinylpyrrolidone K30
PVP K90 Polyvinylpyrrolidone K90

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

Further, in each of the foregoing and following embodiments, it is to be understood that the formulae include and represent not only all pharmaceutically acceptable salts of the compounds, but also include any and all hydrates and/or solvates of the compound formulae or salts thereof. It is to be appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non-crystalline and/or amorphous forms of the compounds.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

Illustrative formats for oral administration include tablets, capsules, elixirs, syrups, and the like. Illustrative routes for parenteral administration include intravenous, intraarterial, intraperitoneal, epidural, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 μg/kg to about 1 g/kg. The dosages may be single or divided, and may administered according to a wide variety of protocols, including q.d. (once a day), b.i.d. (twice a day), t.i.d. (three times a day), or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In addition to the illustrative dosages and dosing protocols described herein, it is to be understood that an effective amount of any one or a mixture of the compounds described herein can be determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The term "patient" includes human and non-human animals such as companion animals (dogs and cats and the like) and livestock animals. Livestock animals are animals raised for food production. The patient to be treated is preferably a mammal, in particular a human being.

In this present disclosure, Col and Cip were for the first time co-encapsulated in anionic liposomes (AL) through $(NH_4)_2SO_4$ gradients. Different methods for measuring the encapsulation efficiency (EE) of Cip and Col were investigated. The effect of anionic lipid and Cip concentration on the encapsulation of Col was studied. The influence of Cip and Col in liposomes on the release of each other was evaluated.

Characterization of Cip/Col Liposomes

The EE and particle size distribution (z-average size and polydispersity index (PDI)) of the liposomes were shown in Table 1. The data showed that the EE of Cip of neutral liposomes (NL) was a little higher than that of the anionic liposome (AL), but without significant difference (p>0.05). It should also be noted that the EEs as determined by these two different methods were in accordance irrespectively to the methods used. However, the encapsulation of Col in NL was much fewer than that in AL. Meanwhile, the EE of Col determined by Method II (Cation-exchange resin mini-column centrifugation) was much lower than that determined by Method I (Centrifugal filtration), and even found to be zero of NL determined by Method II. For AL, the incorporation of Col decreased the EE of Cip slightly from 93.70% to 85.10%, while the existence of Cip at the concentration of 2 mg/mL did not affect the Col encapsulation of AL (DMPG:HSPC=2:3, w/w). Additionally, the encapsulation of Cip and/or Col did not change the size of AL, the average particle sizes were all about 130 nm. The typical morphology of Cip/Col AL was shown in FIG. 2.

TABLE 1

Characterization of Liposomes Containing 2 mg/mL of Col and/or Cip

| | Average | EE of Col (%) | | EE of Cip (%) | |
|---|---|---|---|---|---|
| | diameter/PI | Method I | Method II | Method I | Method II |
| Cip/Col-NL* | — | 5.40 ± 1.41 | 0 | 89.83 ± 3.64 | 89.22 ± 5.47 |
| Cip/Col-AL | 129.9/0.214 | 67.04 ± 5.18 | 18.44 ± 7.15 | 85.19 ± 4.51 | 83.40 ± 4.12 |
| Cip-AL | 131.1/0.184 | — | — | 93.70 ± 3.27 | |
| Col-AL | 129.3/0.207 | 68.75 ± 4.35 | — | — | — |
| Blank-AL | 129.5/0.247 | — | — | — | — |

*NL:DMPG:HSPC = 0:5, w/w; AL:DMPG:HSPC = 2:3

Influence of the DMPG/HSPC Ratio on the Encapsulation of Cip and Col

Figure 3:
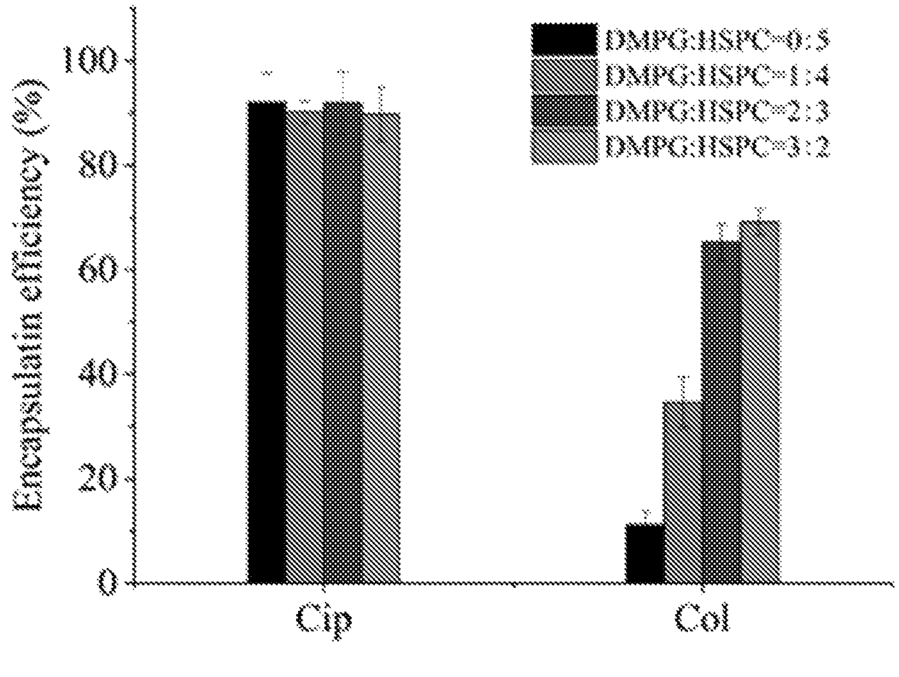
FIG. 3 demonstrates encapsulation efficiencies of Cip and Col in liposomes of various DMPG/HSPC ratios. The EE values were determined by centrifugal filtration method.

As shown in FIG. 3, the EE of Cip was independent to the DMPG/HSPC ratio, on the contrary the EE of Col was greatly related to the content of DMPG incorporated. The EE of Col increased significantly from about 5% to 65% with the increase of DMPG/HSPC from 0:5 to 2:3. But when the DMPG/HSPC ratio went up to 3:2, the encapsulation efficiency (69%) did not further increase compared to that of DMPG/HSPC ratio of 2:3 (P>0.1). Finally, the DMPG/HSPC ratio we chose was 2:3.

Influence of Cip Concentration on the Encapsulation of Cip and Col

One of the most important advantages of remote-loading was that drug can be encapsulated into liposomes with very little loss even at high drug/lipid ratio (17). In this study, with the increase of the Cip concentrations from 2 mg/mL to 12 mg/mL (The Cip/lipid ratios increased from 0.17 to 1.02), no change of the EE of Cip was observed. The EE of Col maintained above 60% with the concentration of Cip from 2 mg/mL to 8 mg/mL, while it sharply decreased to 45.93% when Cip concentration increased to 12 mg/mL (see Table 3).

TABLE 2

Dependence of encapsulation efficiency of Cip and Col on Cip concentrations.

| Cip concentration (mg/mL) | Cip/lipid ratio (mol/mol) | EE of Cip (%) | EE of Col (%) |
|---|---|---|---|
| 2 | 0.17 | 84.51 ± 3.34 | 66.20 ± 3.42 |
| 4 | 0.34 | 87.85 ± 2.28 | 63.49 ± 2.97 |
| 8 | 0.68 | 84.53 ± 2.70 | 63.84 ± 4.13 |
| 12 | 1.02 | 83.64 ± 3.04 | 45.93 ± 3.31 |

*DMPG:HSPC = 2:3, the concentration of Col was 2 mg/mL.

In Vitro Drug Release

To evaluate whether the co-existence of Cip and Col in liposomes would affect the release of each other, the drug release from liposomes containing Cip and Col both at the concentration of 2 mg/mL was measured at 37° C. in PBS (pH 7.4).

Figure 4A:
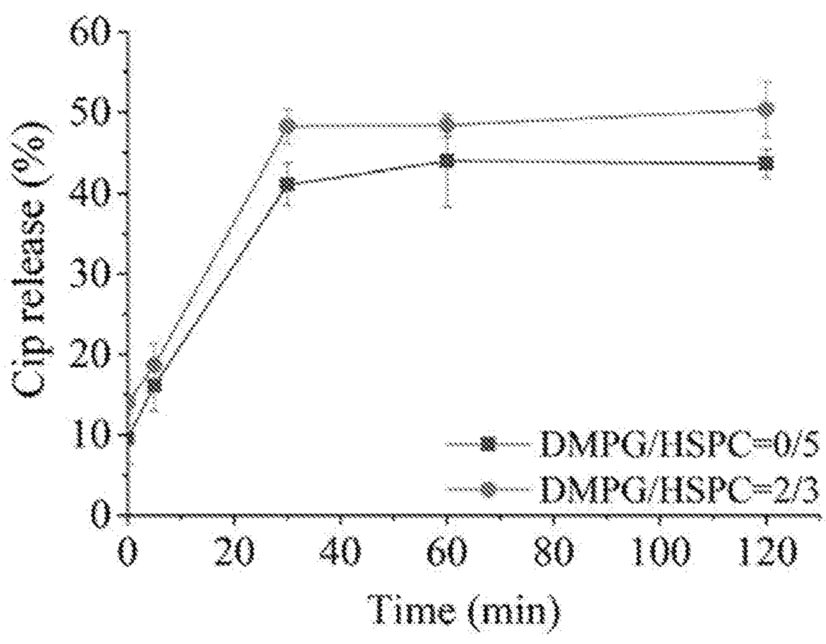
FIG. 4A shows in vitro Cip release profiles of Cip-NL and Cip-AL loaded liposomes (n=3). Red line, DMPG/HSPC=2:3; black line, DMPG/HSPC=0:5.

Release of Cip. The effect of DMPG and Col on the release of Cip of NL (DMPG:HSPC=0:5) and AL (DMPG:HSPC=2:3) were shown in FIGS. 4A-4C, respectively. From FIG. 4A, we can see the release of Cip from AL was similar with that of NL. Rapid release up to 35% was observed within the first 10 min and then remained equilibrium. This rapid release of Cip from liposomes can be attributed to the lack of precipitation of drug in the interior of liposomes (Maurer N, et al., *Biochim Biophys Acta.* 1998, 1374 (1-2): 9-20).

Figure 4B:
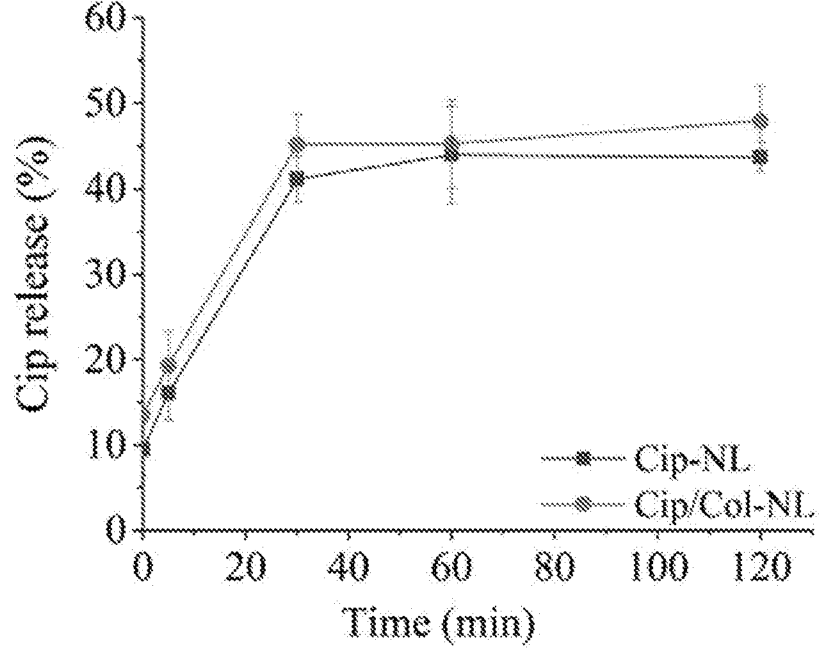
FIG. 4B shows in vitro Cip release profiles of Cip-NL and Cip/Col-NL (DMPG:HSPC=0:5) loaded liposomes (n=3). Red line, Cip-NL; black line, Cip/Col-NL.
Figure 4C:
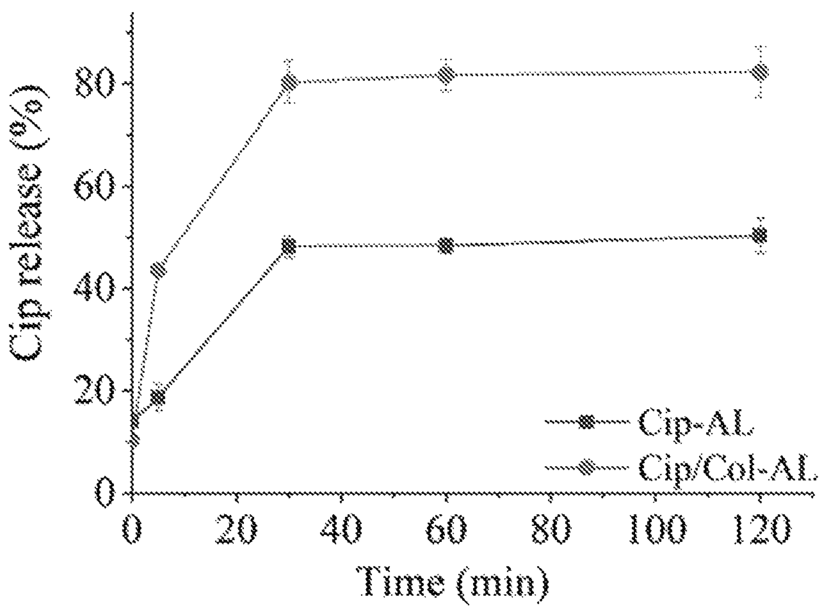
FIG. 4C shows in vitro Cip release profiles of Cip-AL and Cip/Col-AL (DMPG:HSPC=2:3) loaded liposomes (n=3). Red line, Cip-AL; black line, Cip/Col-AL.

Wallace et al reported that Col could accelerate the release of co-formulated Azithromycin from liposomes (Wallace S J, et al., *J Pharm Sci.* 2013, 102:1578-1587). While in this study, only 5% Col was encapsulated in liposomes (FIG. 3), which had no obvious influence on the release of Cip from NL (FIG. 4B). Due to the high Col encapsulation of about 65%, Col significantly increased the release of Cip from AL as shown in FIG. 4C. Compared to Cip-AL, more than 30% of Cip was released from Cip/Col-AL at time zero, and the release plateau climbed to 80% at about 30 min.

Determination of the Encapsulation Efficiency

Figure 6A:
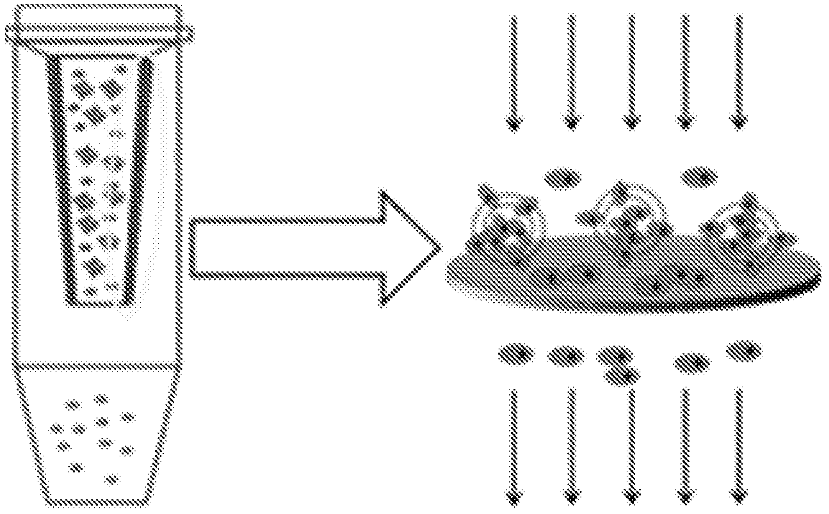
FIG. 6A is a schematic diagram of centrifugal filtration method for the separation of free drugs from liposome suspension.
Figure 6B:
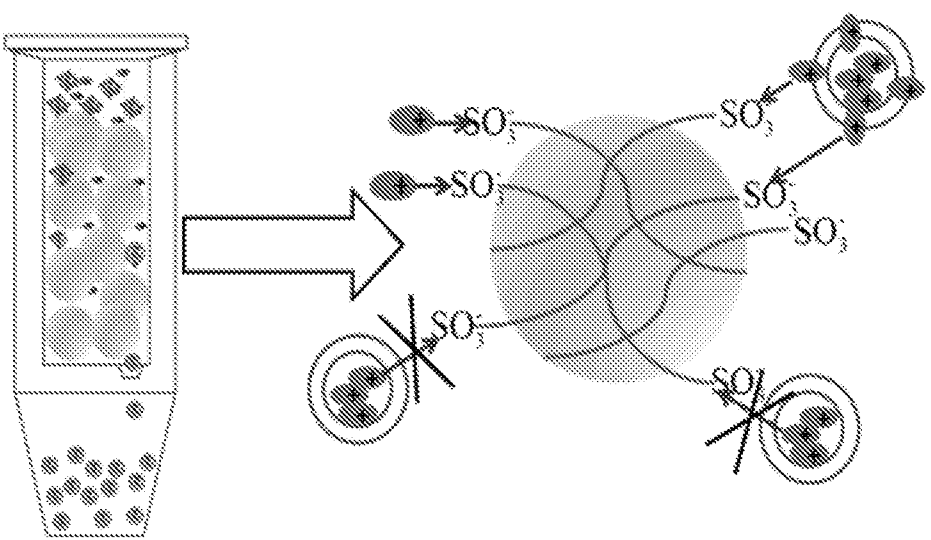
FIG. 6B is a schematic diagram of cation-exchange resin column centrifugation method for the separation of free drugs from liposome suspension.

Various methods were utilized to determine the encapsulation efficiency of liposomes. In this study, centrifugal filtration (Method I) and ion-exchange resin column centrifugation (Method II) were used to separate free drug from liposomes in the determining the drug encapsulation efficiency of liposomes, and the mechanism of both methods were illustrated in FIG. 6. For the centrifugal filtration method (FIG. 6A), the free drug dissolved in the outer aqueous phase flowed across the pores of the membrane filter and was found in the filtrate after centrifugation, while the encapsulated drug, whether entrapped in the inner aqueous phase or associated with the lipid bilayer, was cut off by the membrane filter. Dowerx® 50WX4 is a kind of strong acid (sulfonic acid) type of cation-exchange resin, cationic molecules can associate to the resin via exchange with hydrogen ions. For the second method (FIG. 6B), when passing through the column packed with cation-exchange resin, both the free cationic drug and the drug associated to the liposomes with the cationic residues located on the outside surface of the liposomes can be absorbed on the resin, only the drug encapsulated in the inner aqueous phase can be eluted through the column. Cation-exchange resin column centrifugation method was normally applicable for the separation of cationic drug from liposomes (Storm G., et al., *BBA-Biomembranes* 1985, 818:343-351).

The EEs of various liposomal formulations were determined with both methods as provided in Table 1. Based on the difference between the encapsulation efficiencies determined by these two methods, we can make sure whether the drug molecules were entrapped in the inner aqueous phase or just associated with the lipid bilayer membrane, thus deduce its distribution in the liposomes.

Co-Encapsulation of Cip and Col into Liposomes

As the amphiphilic and weak basic nature of Col and Cip, the co-capsulation of Col and Cip became a great challenge. Passive encapsulation methods, such as dry lipid film, freeze drying, and other methods were widely investigated to load Col into liposomes. The encapsulation efficiencies of Col varied greatly ranging from 5% to 50% with passive encapsulation method as reported in literatures (Wallace S J, et al., *J Pharm Sci.* 2012, 101:3347-3359). A remote loading method, i.e. $(NH_4)_2SO_4$ gradient method, was found to be effective in loading Cip into liposomes with high EEs.

At the beginning of this study, we tried to encapsulate Col passively into liposomes using dry lipid film method, and at the same time establish a transmembrane $(NH_4)_2SO_4$ gradient for further remote loading of Cip. In such procedure, the lipid film was hydrated with $(NH_4)_2SO_4$ solution containing Col, and the EE value of Col directly determined by Method I was about 35%. But, after passing the Col loaded "blank" liposomes through a Dowerx® 50WX4 cation-exchange spin column to build the $NH_4^+$ gradient, it was found that Col was entirely adsorbed onto the cationic-exchange resin, and the amount of Col loaded into liposomes could not be detected. In the subsequent investigations, a modified procedure was introduced to co-encapsulate Cip and Col into liposomes, i.e. the lipid film was firstly hydrated with $(NH_4)_2SO_4$ solution free of Col, after passing the blank liposomes through cation-exchange spin column to build the $NH_4^+$ gradient, the gradient liposomes were incubated together with Col and Cip solution to load both drugs at the same time.

Figure 9:
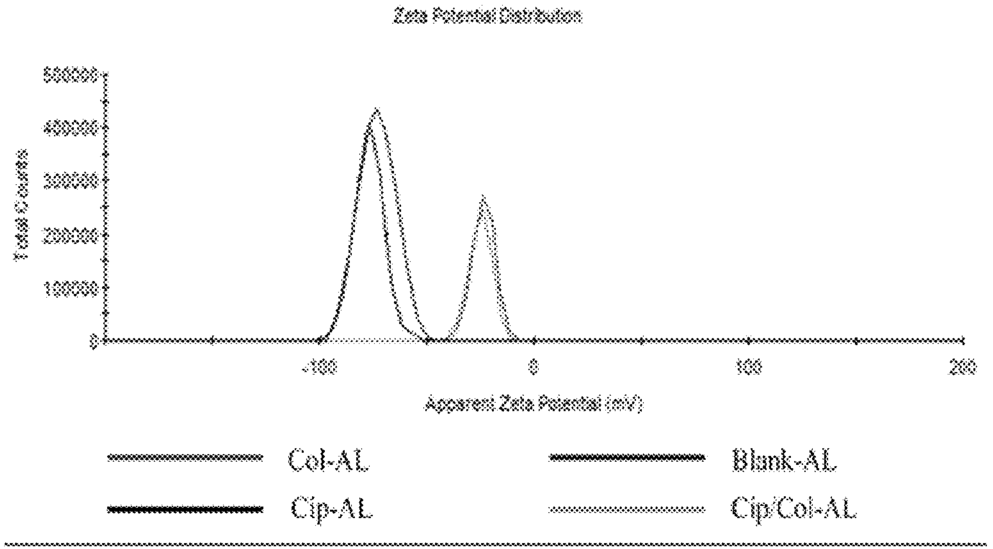
FIG. 9 shows Zeta potential distribution of Cip and/or Col liposomes (DMPG:HSPC=2:3).

As shown in Table 1, NL or AL had approximately the same encapsulation efficiencies of Cip, and the values determined with the two different methods were very similar From these results, we concluded that Cip was mainly loaded through the $(NH_4)_2SO_4$ gradient into the inner aqueous phase of liposomes, less or no Cip was associated to the outside surface of the liposomes via ionic interaction between Cip and DSPG as illustrated in FIGS. 7A-7B. According to this result, the incorporation of Cip had no effect on the zeta potential of anionic liposomes (FIG. 8 and FIG. 9).

On the contrary, the EE of Col of NL was obviously lower than that of the AL, and interestingly, the centrifugal filtration method gained significantly higher EE of Col. EE of Col in NL indicated that only 5.40% of Col was associated to NL, and no Col entered the inner aqueous phase of NL (Col was not detected after passing the liposomes through the ion-exchange resin column, see Table 1). The result revealed Col can't be effectively loaded into liposomes through $(NH_4)_2SO_4$ gradients and just associated to liposome surface via weak hydrophobic interaction between the hydrophobic acyl chain of Col and the lipid membrane as illustrated in FIG. 7A, which was in accordance with the observations of Mestresa et al (Mestres C, et al., *Int J Pharm.* 1998, 160:99-107). But, such hydrophobic interaction between the drug and neutral lipid membrane may be extremely weak. Elaine et al investigated the morphology changes of neutral liposomes after exposure to polymyxin with freeze-fracture electron microscope, as no perturbations to the lipid membrane was observed, the authors disclosed little interaction of polymyxin with neutral lipid membrane (Bearer E L, et al., *Proc Natl Acad Sci.* 1980, 77:6601-6605).

Incorporation of anionic lipid into the liposomes (DMPG: HSPC=2:3) markedly increased EE of Col (67.04% by method I and 18.44% by method II). The result also indicated that about 48.60% Col was associated with lipid bilayer, which can be easily adsorbed by the cationic-exchange resin. Considering of the structure of Col (FIG. 1B), this part of Col might distribute on liposomes with hydrophobic acyl chain inserted in the lipid bilayer and the positively charged hydrophilic residue exposed on the outer-surface of liposomes (FIG. 7B). While 18.44% of Col that resided in liposomes even after passing through the cationic-exchange resin column might locate in the inner aqueous phase (FIG. 7B). As described above, Col was added after the formation of liposome in the remote-loading process in this study, so how can the ionized molecules of Col penetrate across the lipid bilayer and enter the inner aqueous phase of liposomes except driving by $(NH_4)_2SO_4$ gradients? A possible answer may be found from Deris's studies on the penetration of polymyxin lipopeptides into Gram-negative bacteria (Conly J M, et al, *Can J Infect Dis Med.* 2006, 17:267-269): the electrostatic interactions weaken the stability of the outer membrane, and then the hydrophobic insertion destabilizes the outer membrane through hydrophobic expansion, and finally polymyxin went into the inner aqueous phase and associated to the inner lipid membrane.

In Vitro Drug Release

Interaction of Col with liposomes and its influence on drug release. From FIG. 3, we can see the EE of Col relied on the content of DMPG in lipid. In this study, zeta potential was used to characterize the interaction of Col with DMPG. FIG. 8 illustrated the zeta potential of blank liposomes without DMPG was −3.62 mV, the incorporation of Cip and Col did not change the zeta potential. The incorporation of negatively charged lipid, DMPG, to the blank liposomes decreased the zeta potential sharply to about −56 mV (DMPG/HSPC=1:4), −74 mV (DMPG/HSPC=2:3), and −76 mV (DMPG/HSPC=3:2), respectively, but the potentials of the last two formulations showed no significant difference. Interestingly, after addition of Cip and Col, the potential of all anionic liposomes decreased to about −30 mV. To verify the interaction of negatively charged liposomes with Col, the zeta potential of AL (DMPG/HSPC=2:3) encapsulated with Col and/or Cip was measured separately. In FIG. 9, Cip liposomes had the similar potential to blank liposomes, while the zeta potential distribution curves of Col liposomes and Cip/Col liposomes almost overlapped, the peak value shifted from −74 mV (blank liposomes) to −26 mV. This result was consistent with the encapsulation result (FIG. 3) indicating that electrostatic interaction with liposomes played a pivotal role in the encapsulation of Col.

Figure 4D:
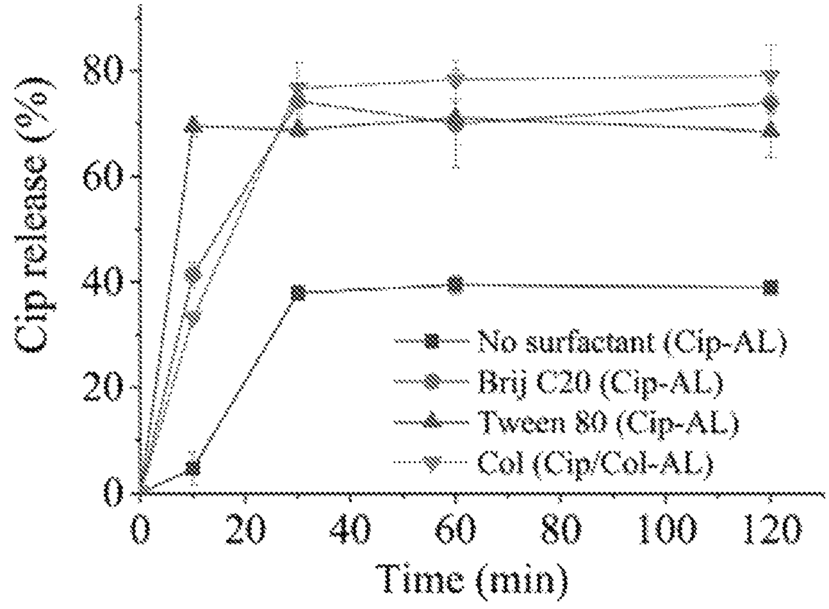
FIG. 4D shows in vitro Cip release profiles of Cip-AL and Cip/Col-AL (DMPG:HSPC=2:3) loaded liposomes (n=3). Red line, Brij C20 (Cip-AL); black line, no surfactant (Cip-AL); Blue line, Tween 80 (Cip-AL); Green line, Col (Cip/Col-AL) (n=3, mean±SD).
Figure 5:
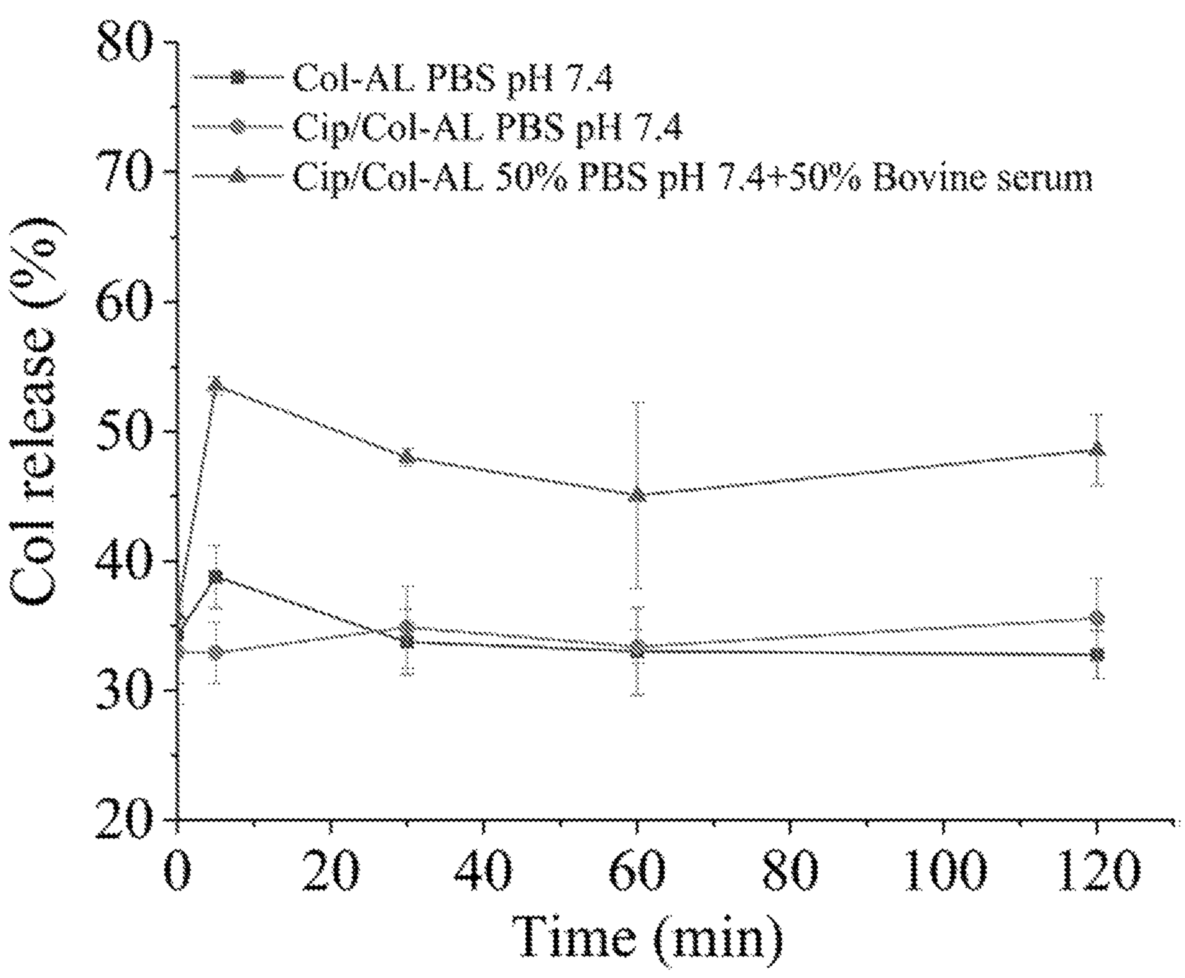
FIG. 5 shows in vitro release profiles of Col from Col-AL or Cip/Col-AL in different release media (DSPG/HSPC=2:3) (n=3, mean±SD) with or without Cip. Different to the release of Cip, there was no Col released from liposomes throughout the sample period of 120 min, and the co-encapsulation of Cip had no influence on the release of Col.
Figure 10A:
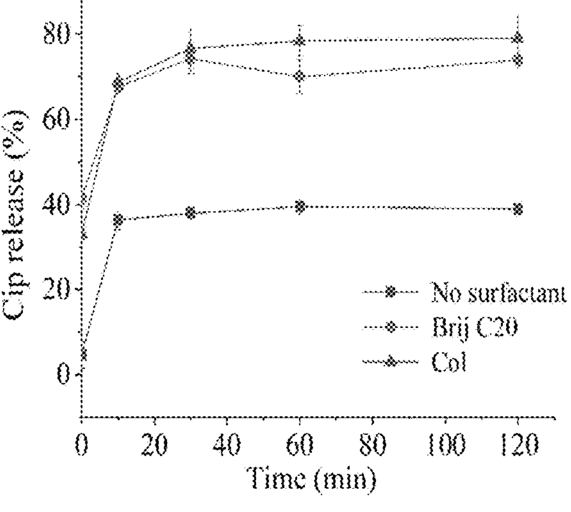
FIG. 10A demonstrates in vitro Cip release profiles of Cip-AL with (DMPG/HSPC=2:3) (n=3)
Figure 10B:
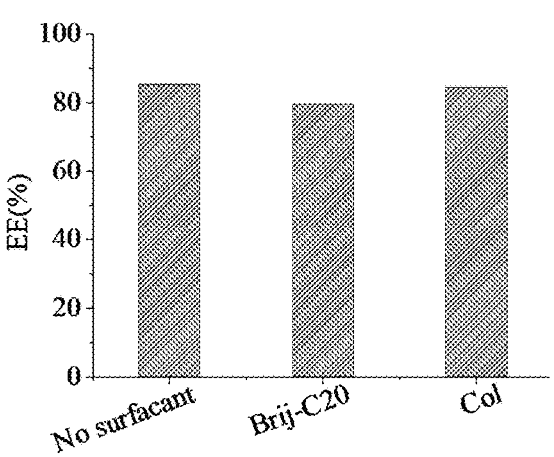
FIG. 10B shows in vitro encapsulation efficiency of Cip-AL with (DMPG/HSPC=2:3) (n=3).

Surfactant-like effect of Col on the release of Cip. FIG. 4C clearly indicated that the incorporation of Col accelerated the release Cip from AL. It is known that Col acted as a detergent-like fashion in killing bacteria, it strongly interacted with phospholipids of the cell membrane leading to a loss of integrity of the membrane and an increase in the permeability of the cell envelope, leakage of cell contents, and subsequently cell death (Conly J M, et al., 2006). In this study Brij C20, was incorporated into the liposomes with the concentration of 0.2% (g/mL) instead of Col, and the influence on Cip release was investigated as in FIGS. 4D and 10A. The encapsulation efficiencies of Cip-L with Brij C20 didn't decreased (FIG. 10B), which mean that the surfactant at low concentrations (0.2%) couldn't not cause the disruption of the liposomes. From FIG. 10A we can see the release curve of Cip/Col-L was similar with the liposome with Brij C20.

Particle Density

Powder true, bulk and tapped densities of selected formulations were listed in Table 4. Clearly, the porous structure of USFD formulations (as shown in the SEM images) contributes to the low bulk and tapped densities. All the densities decreased with the increase in dilution factors before USFD (F1 did not dilute, F8 and F9 diluted 2 folds, and F11 diluted 3 folds). This indicates that solid concentration of UFSD feed solution has a significant impact on powder bulk density/porosity, which leads to substantial influence on powder aerosolization.

TABLE 3

True, bulk and tapped densities of liposomal powder formulations (mean ± SD, n = 3)

| | True density ($g/cm^3$) | Bulk density (g/mL) | Tapped density (g/mL) |
|---|---|---|---|
| F1 | 1.417 ± 0.000 | 0.335 ± 0.026 | 0.498 ± 0.046 |
| F8 | 1.168 ± 0.003 | 0.051 ± 0.004 | 0.086 ± 0.004 |
| F9 | 1.191 ± 0.000 | 0.057 ± 0.004 | 0.096 ± 0.015 |
| F11 | 0.931 ± 0.000 | 0.039 ± 0.002 | 0.065 ± 0.008 |

Cytotoxicity Study

Figure 12:
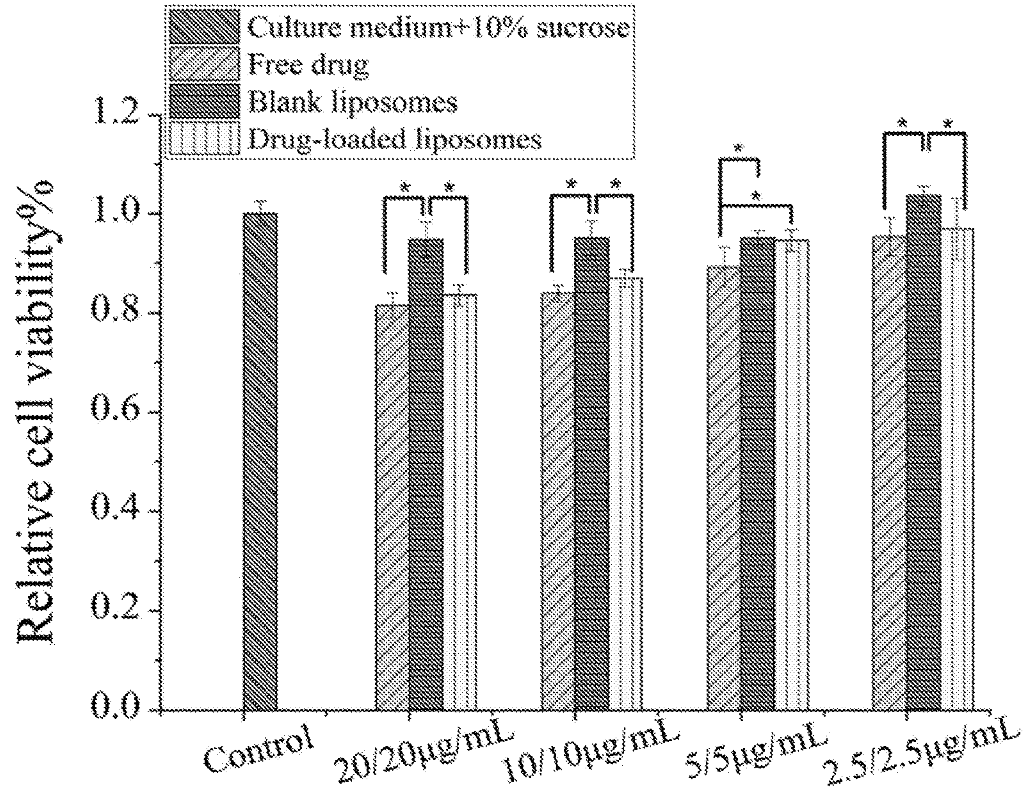
FIG. 12 depicts cytotoxicity of free drugs, blank liposomes and Cip/Col-AL liposomes (DSPG/HSPC=2:3) in A549 human airway cells (n=3, mean±SD). Notes: One-way ANOVA, followed by Dunnett's multiple comparison test, was performed to calculate statistical significance. *: significant difference, $P<0.05$.

Cell viability data of the selected liposome formulation was showed in FIG. 12. For the blank liposome, there is almost no inhibitory effect on the cell viability showing no cytotoxicity. Therefore, the lipid materials used in the liposome formulation appear safe for use in pulmonary drug delivery. The drug-loaded liposomes have comparable cell viability to those of free drugs and blank liposomes, suggesting no apparent cytotoxicity to the human airway epithelial cells.

In Vitro Antimicrobial Activities

According to our previous studies, two studied clinical isolates were resistant to both colistin and ciprofloxacin. For *P. aeruginosa* H131300444, the MICs of colistin and ciprofloxacin are 128 and 8 mg/L. For *P. aeruginosa* H133880624, the MICs of colistin and ciprofloxacin are 128 and 16 mg/L.

Figure 13A:
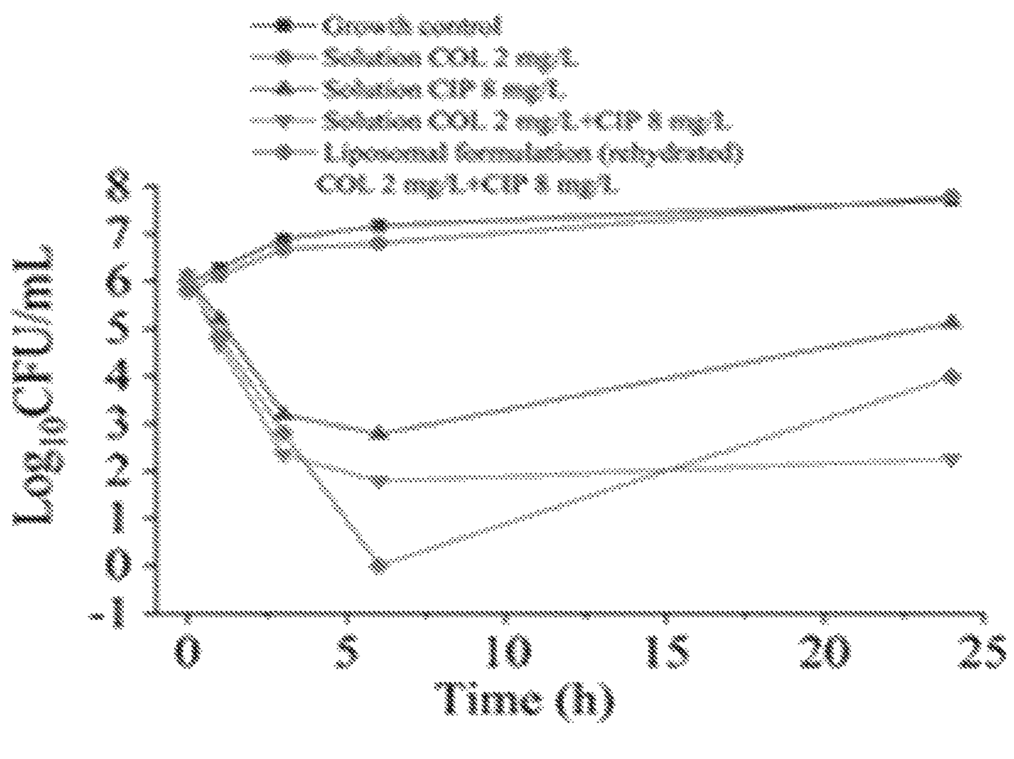
FIGS. 13A-13B show static time-kill kinetics for colistin and/or ciprofloxacin against *P. aeruginosa* H131300444 (FIG. 13A) and *P. aeruginosa* H133880624 (FIG. 13B). The limit of detection is 1.30-$\text{Log}_{10}$ CFU/mL (equivalent to one colony per plate).
Figure 13B:
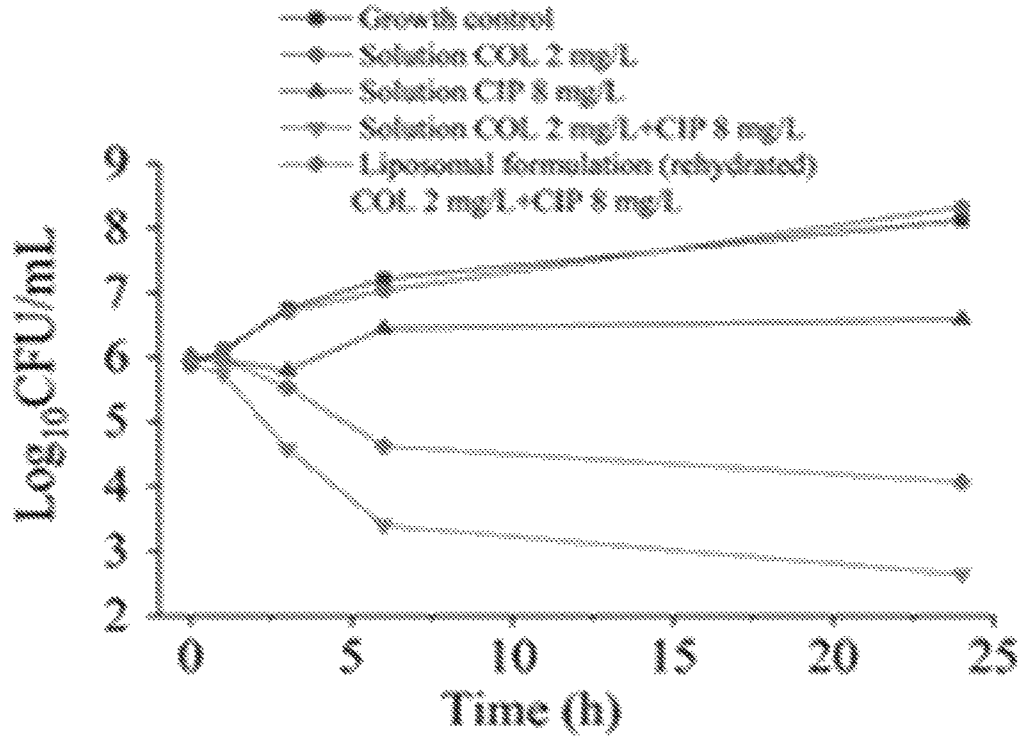
Figure 14A:
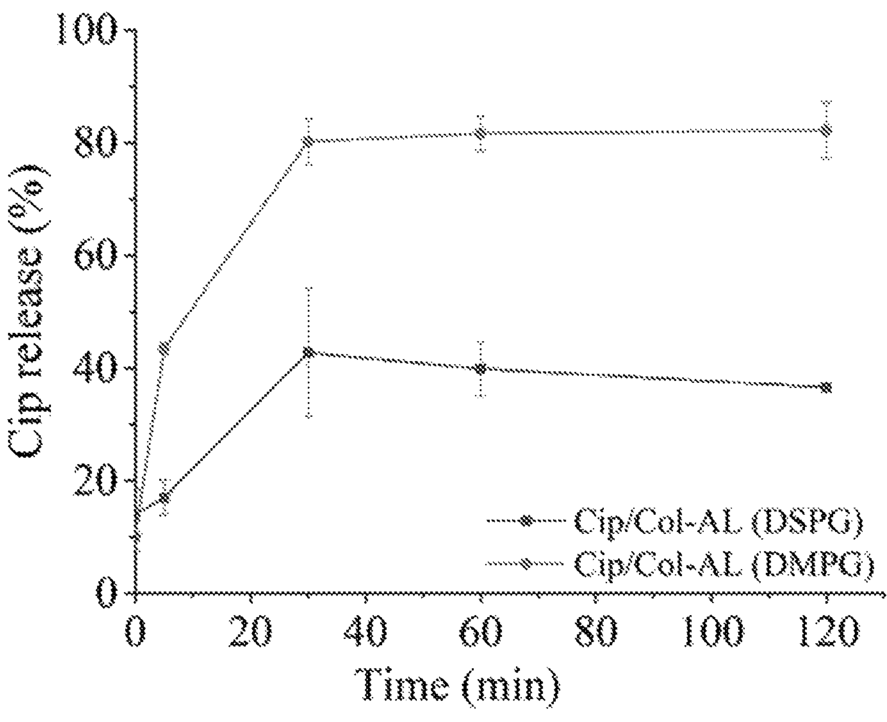
FIGS. 14A-14B depict the ciprofloxacin release profiles of Cip/Col-AL containing different phospholipids in PBS (FIG. 14A) and the ciprofloxacin release profiles of Cip/Col-AL containing DSPG in different release media (FIG. 14B) (n=3, mean±SD).
Figure 14B:
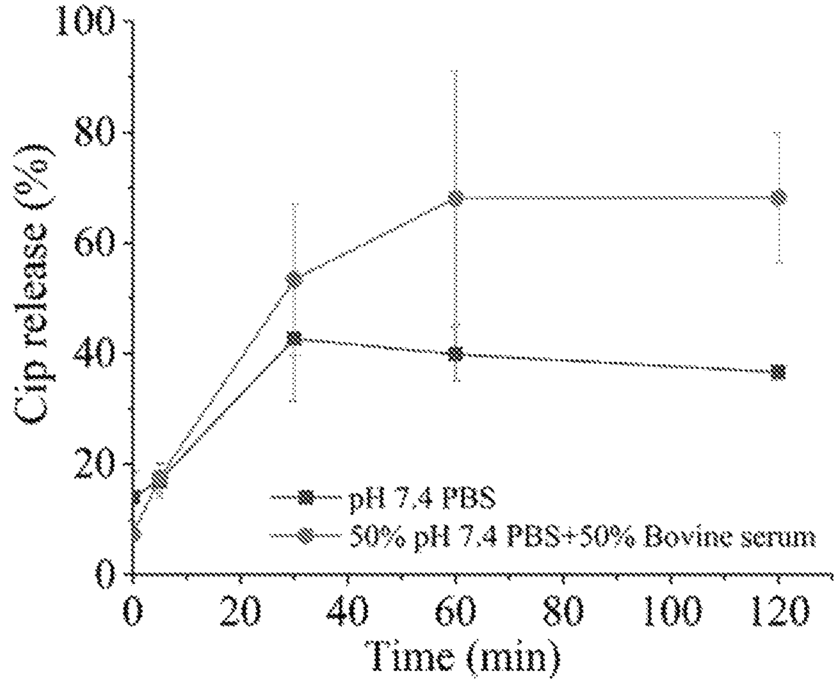

FIGS. 13A-13B showed the time-kill profiles of colistin and ciprofloxacin solution and liposomal formulation (rehydrated). Colistin (2 mg/L) monotherapy showed no antibacterial effect against *P. aeruginosa* H131300444 and *P. aeruginosa* H133880624. Ciprofloxacin (8 mg/L) monotherapy showed bacterial killing for both clinical isolates, albeit regrowth was observed in 6 hrs for *P. aeruginosa* H133880624. The combination solution of colistin and ciprofloxacin (2 and 8 mg/L) demonstrated superior antibacterial activity than the monotherapy. For *P. aeruginosa* H131300444, liposomal formulation showed more rapid killing than the combination solutions in 6 hrs. For *P. aeruginosa* H133880624, it is noteworthy that both combination solutions and liposomal formulation (rehydrated) resulted significant killing of bacteria without any regrowth in 24 hrs.

To summarize, a remote loading method using an ammonium sulfate gradient was proved to be effective in loading Cip into liposomes with high EEs. The Col was associated with anionic liposomes via electrostatic attraction. The size of liposomal particles was 130 nm and the EE of Cip and Col was 85.19±4.51% and 67.04±5.18%, respectively. The EE of Cip was independent to the DMPG/HSPC ratio, on the contrary, the EE of Col was greatly related to the content of DMPG. The incorporation of Cip had no effect on the release of Col, however, the incorporation of Col could significantly accelerate the release of Cip from anionic liposomes. The combination of Cip and Col may offer a viable alternative treatment option for eradicating *P. aeruginosa*. However, further studies are required in bacterial killing and animals.

Materials and Methods

Hydrogenated soybean phosphatidylcholine (HSPC), 1,2-Distearoyl-sn-glycero-3-phosphoglycerol, sodium salt (DSPG-Na), 1,2-Dimyristoyl-sn-glycero-3-phosphoglycerol, and sodium salt (DMPG-Na) (stored at −20° C.) were obtained from NOF America Corporation (White Plains, NY, USA). Cholesterol, Brij C20 and Tween 80 were purchased from Sigma (St. Louis, MO, USA). Ammonium sulfate was obtained from Alfa Aesar (Ward Hill, MA, USA). Colistin sulfate and ciprofloxacin hydrochloride monohydrate was purchased from Betapharma Co. Ltd. (Wujiang, Shangai, China). Dowerx® 50WX4, ion-exchange resin (200~400 mesh) was obtained from Acros Organics (Geel, Belgium). 3-(4,5-dimethylthiazol-2-yl)-2,5-diphenyltetrazolium bromide (MTT) was obtained from Invitrogen (Life Technologies Corporation, Eugene, OR, USA). Penicillin streptomycin (10,000 U/mL penicillin, 10,000 μg/mL streptomycin), F-12 K nutrient mixture, fetal bovine serum (heat inactivated) and 0.5% trypsin-EDTA were purchased from Gibco (Life Technologies Corporation, Eugene, OR, USA). All reagents and chemicals used for HPLC analysis were of HPLC grade.

Preparation of Drug Loaded Liposomes

HSPC, DSPG, DMPG and cholesterol (lipids:cholesterol=3:1, w/w) were weighed into an evaporating flask and dissolved in chloroform. The solvent was then evaporated at reduced pressure to form a dry lipid film. The film was hydrated in 300 mM $(NH_4)_2SO_4$ at 65° C. The resulting suspension of multilamellar liposomes (lipid concentration of 5% w/v) were then ultrasonicated with an ultrasonic probe (Sonifier 250, Branson Ultrasonics Corporation, Danbury, CT USA) and extruded through polycarbonate membrane of 200 nm pore size to yield unilamellar liposomes (LUVs). A trans-membrane $NH_4^+$ gradient across the bilayer of LUVs was generated after removing the extra liposomal $NH_4^+$ by passing the liposome suspension through a Dowerx® 50WX4 cation-exchange spin column (pre-equilibrated with 10% sucrose aqueous solution). The LUVs suspension was mixed with the solution of Cip and/or Col, the mixture was incubated at 60° C. for 10 min for drug loading.

Preparation of Ciprofloxacin-Colistin-Loaded Liposomes Dry Powder

Figure 11:
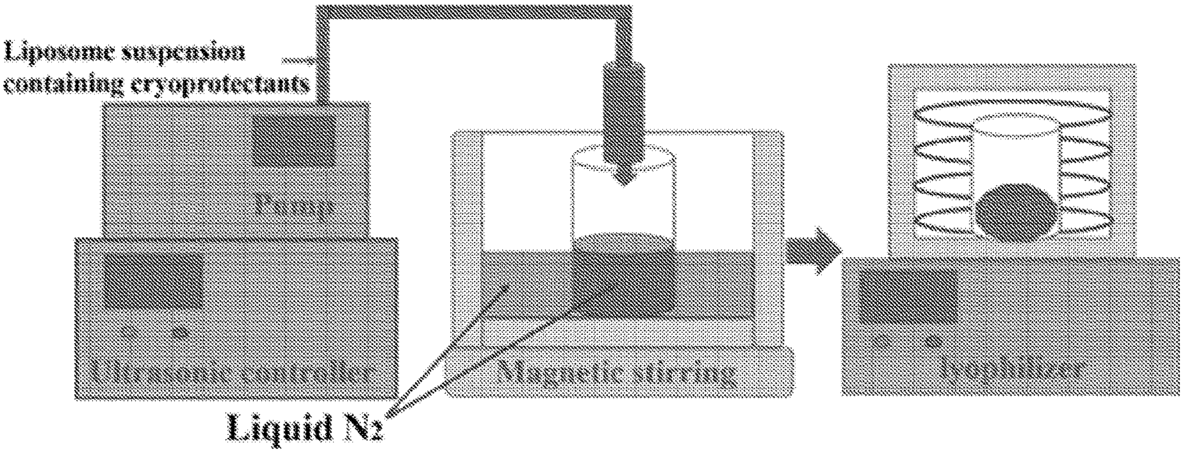
FIG. 11 shows a schematic diagram of the apparatus and the process of ultrasonic spray freeze drying.

The liposomal dry powder was prepared by the ultrasonic spray freeze drying (USFD) (Bittner and Kissel, J. Microencapsulation 1999, 16, 325-341; Yin F. et al., Int. J. Nanomed. 2014, 9, 1665-1676). Before USFD, the cryoprotectants (Table 5) were added to the liposomal suspension, which was denoted as "external cryoprotectant". Aqueous solutions were fed via a pump (1B.1003-R/65, Petro Gas ausrüstungen Berlin GmbH, Berlin, Germany) at 1.0 mL/min into the ultrasonic nozzle which was controlled at 3.5 watt by an ultrasonic controller (BÜCHI Labortechnik AG, Flawil, Switzerland). The atomized fine droplets were sprayed into a glass beaker containing liquid nitrogen. The nozzle was positioned at 10 cm above the liquid nitrogen surface. Following atomization, the excess liquid nitrogen was evaporated, and the frozen droplets were dried for 48 hrs in a lyophilizer (Labconco FreeZone, Kansas, MO, USA). The freeze dryer was set at −52° C. and the vacuum was 0.014 mbar. The apparatus and process of USFD are shown in FIG. 11. Freeze dried powders were collected and stored in a sealed vial with desiccant at 20° C. For characterization of the reconstituted Cipro-Col-Lips dry powder, the formulations were added into Milli-Q water to form the liposome suspension.

Assay of Ciprofloxacin and Colistin

The HPLC system consisted of G1311C pump (1260 Quat Pump VL), G1330B thermostate (1290 Thermostate), G1329B autosampler (1260 ALS), G1316A thermostated column compartment (1260 TCC), and G1314F variable wavelength detector (1260 VWD) (Agilant, Waldbronn, Germany) was used for the analysis of ciprofloxacin and colistin. The chromatographic separation was performed using an Agilant Eclipse Plus C18 column (150 mm×4.6 mm, 5 μm, Agilant, Waldbronn, Germany). The isocratic mobile phase was a mixture of 30 mM solution of sodium sulfate (adjusted to pH 2.5 with $H_3PO_4$) and acetonitrile (76:24, v/v). Sample was eluted at a flow rate of 1.0 mL/min, and the detection wavelength was set at 215 nm. The calibration curve was linear ($r^2>0.999$) over the concentration range of approximately 0.006 to 0.22 mg/mL for Cip and approximately 0.5 to 0.006 mg/mL for Col.

TABLE 4

Formulations of liposomes and ultrasonic spray freeze drying powders.

| Formula* | Hydrated solution | Added cryoprotectants before USFD |
|---|---|---|
| F1 | 10% S + 0.5 | 10% S |
| F2 | mol/L AS | 10% T |
| F3 | | 7% M |
| F4 | 0.5 mol/L AS | 15% M + 5% S |
| F5 | | 15% M + 5% S |
| F6 | 10% S + 0.5 | 10% M + 5% L |
| F7 | mol/L AS | 10% M + 10% L |
| F8 | | 15% M + 5% L |
| F9 | 5% M + 0.5 | 10% M + 5% S + 5% L |
| F10 | mol/L AS | 10% M + 5% T + 5% L |
| F11 | | 10% M + 5% S + 5% L |
| F12 | | 10% M + 5% S + 5% L |

*The volume of formulations (F5-F10) were diluted two-fold before USFD. The volume of formulation 11 was diluted three-fold before USFD. The volume of formulation 12 was diluted four-fold before USFD. S means sucrose, T means trehalose, M means mannitol and AS means ammonium sulfate.

Encapsulation Efficiency

For determination of the encapsulation efficiency, liposome suspension was diluted 2-fold with 10% sucrose aqueous solution, and the free drug and drug encapsulated in the liposomes were separated using two different methods as described below.

Method I—Centrifugal filtration. 0.5 mL of liposome suspension was transferred to Amicon® Ultra centrifugation filter (MWCO: 50 KDa, Merck Millipore Ltd, Tullagreen, CarrigtwohillCo Cork, Ireland), and centrifuged at 5000 rpm for 30 min using a MX-200 Centrifuge (Tomy Kogyo Co. LTD, Tokyo, Japan) (21). The unencapsulated drug was recovered in the filtrate, and the free drug content, $M_{free}$, was quantified by HPLC. The liposome suspension was diluted 10-folds with 70% methanol (containing 0.02 mol/L HCl) and analyzed by HPLC to determine the total drug content, $M_{total}$. The encapsulation efficiency, EE (%), was determined as $$EE\ (\%) = (M_{total} - M_{free})/M_{total} \times 100\% \quad \text{(Eq. 1)}$$

Method II—Cation-exchange resin mini-column centrifugation. The mini-column was prepared by packing Dowex® 50WX4 cation-exchange resin in a 3 ml plastic syringe lined with glass wool in the bottom of the barrel (22). The column was placed in a test tube and spun at 3000 rpm for 3 min to remove excess buffer. The liposome suspension was diluted 2-fold with 10% sucrose aqueous solution, and 0.1 ml of the diluted suspension was transferred to the top of the column. The column was centrifuged at 3000 rpm for 3 min, followed by addition of 0.1 ml of 10% sucrose aqueous solution on top of the column and centrifugation for another 3 min. The elute was collected and diluted 10-fold with 70% methanol (containing 0.02 mol/L HCl), and the drug encapsulated in liposomes, $M_{lip}$, was assayed by HPLC. The total drug content, $M_{total}$, was separately determined with the same procedure as described in the Method I. The encapsulation efficiency, EE (%), was determined by Eq. 1.

In Vitro Drug Release

In this study, phosphate buffered saline (PBS pH 7.4) was selected as the dissolution media. PBS can be a suitable simple alternative dissolution media for this early-stage study and has been widely used in in-vitro dissolution studies (Pharmaceutical Research, August 2012, Volume 29, Issue 8, pp 2157-2166; European Journal of Pharmaceutics and Biopharmaceutics, Volume 70, Issue 1, September 2008, Pages 145-152). A 2 mL aliquot of liposome suspension containing approximately 2 mg/mL Cip and/or 2 mg/mL Col was mixed with 8 mL of PBS pH 7.4 at 4° C. Immediately, 0.2 mL of sample was withdrawn for the determination of the total drug content at time zero, and another 0.5 mL of sample was transferred to Amicon® Ultra centrifugation filters (MWCO: 50 KDa) and the free drug content was determined according to Method I in the Section of Encapsulation efficiency. The remaining liposomal suspension was then incubated in water bath at 3TC and stirred gently for 2 h. An aliquot of 0.5 mL of samples was withdrawn at 10 min, 30 min, 60 min, and 120 min, respectively, and the free drug contents were determined subsequently. In vitro drug release test of each formulation was performed in triplicate, and data was represented as mean±standard deviation.

Due to the presence of unencapsulated drug in liposomes, the normalized release rate was calculated as:

$$100(M_T - M_b)/(100 - M_b), \quad \text{(Eq. 2)}$$

wherein $M_b$ is the percent of free drug before dilution with PBS; $M_T$ is the percent of free drug determined at different time point after diluted by PBS.

Particle Size and Zeta Potential Measurement

Particle size and zeta potential of the liposomes were determined using a Malvern Zetasizer Nano ZS90 (Malvern Instruments Inc., Malvern, UK). For the measurement of particle size, liposomes were dispersed in deionized water, while for the measurement of zeta potential, liposomes were dispersed in phosphate buffer solution pH 7.4 (5 mM). Three samples of each formulation were made, and the data was reported as mean±SD of the triplicate measurements.

Transmission Electron Microscopy (TEM)

The TEM images of the liposomes were obtained using a Hitachi H-7600 Electron Microscope (Hitachi, Japan) at 30,000× operating at 80 kV. Briefly, a dilute suspension of liposomes was pipetted on carbon coated copper grids, after 1 min of incubation, the excess sample was removed, followed by negative staining with 1% aqueous uranyl acetate solution. The stained grid was dried in air before observation.

Morphology of liposomal suspensions before USFD were evaluated by cryo-TEM. Liposomes suspension (3 μL) was placed on a TEM copper grid covered with a perforated carbon film and then blotted with filter paper to obtain a thin aqueous film. The grid was vitrified immediately by plunging the grid (kept at 100% humidity and 22° C.) into liquid ethane maintained at its melting point using a Vitrobot (FEI Company, Hillsboro, OR, USA). The vitreous films were transferred to a Talos TEM (FEI Company, Hillsboro, OR, USA) using a Gatan cryotransfer (Gatan, Pleasanton, CA, USA), and the samples were observed in a low-dose mode. Images were acquired at 300 kV at a temperature around −173° C. with a charge-coupled device camera (FEI Company, Hillsboro, OR, USA).

The morphology of Cipro-Col-Lips dry powder prepared using the USFD method was obtained by the scanning electron microscope (SEM, NOVA nanoSEM, FEI Company, Hillsboro, OR, USA) at 5.0 kV. Each formulation powder was poured on a carbon sticky tape and attached to the metal stubs. The stubs were then placed in a sputter coater (208 HR, Cressington Sputter Coater, England, UK) to obtain gold coating at 40 mA for 90 s to achieve a coating thickness of 10-40 nm.

Particle Density

The true density ($\rho_1$, excluding open pore and closed pore volumes) of the ultrasonic spray freeze dried powder was analyzed by helium pycnometry (AccuPyc II 1340 Pycnometer, Micromeritics Instrument Corp., Norcross, GA, USA) using a 1.0 $cm^3$ sample cup. Samples were weighed before analysis and were purged with helium gas before analysis. Bulk density ($\rho_2$) and tapped density ($\rho_3$) measurements were performed as previously described (Zhou Q, et al., *Int. J. Pharma.* 2011, 413, 36-43; Zhou Q, et al., *Powder Technol.* 2011, 207, 414-421). Samples were gently poured into a 10 ml measuring cylinder via a funnel at a fixed height and bulk volume recorded. The relatively small cylinder of 10 ml was used here due to the small volume of our samples. The graduated cylinder was tapped for 1000 taps by an automatic tapper (AUTOTAP™, Quantachrome Instruments, Boynton Beach, USA) and the tapped volume recorded. The tapper operated with a 3.18 mm vertically travel at a tapping speed of 260 tap/min. Each measurement was run in triplicate.

Dynamic Vapor Sorption

Moisture sorption profiles for the spray freeze dried formulations were obtained by dynamic vapor sorption (DVS-Intrinsic, Surface Measurement Systems Ltd., London, UK). The chamber was kept at 25° C. under continuous nitrogen flow. The USFD powder (approximately 10 mg) was analyzed in the measurement chamber at the relative humidity (RH) from 0% to 90%. The powder sample was equilibrated at 0% relative humidity (RH) to provide a baseline, then to raise the humidity in steps of 10% RH to 90% RH at 25° C. for sorption and 90% RH to 10% RH for desorption.

Powder X-Ray Diffraction (PXRD)

Diffraction patterns of the powder samples were measured using an X-ray powder diffractometer (Empyrean, Malvern Panalytical B.V., Longmont, CO, USA) with a scan speed of 0.2°/s. The Cu anode X-ray tube was operated at 45 kV and 40 mA in combination with a Ni filter to give monochromatic Cu-Kα X-rays. Measurements were generally taken from 5 to 60° on the 2θ scale at a step size of 0.01° per second.

In-Vitro Aerosol Performance Study

The aerosolization behavior of each powder formulation was measured using a Multi-Stage Liquid Impinger (MSLI) (Copley Scientific Limited, Nottingham, UK) with a USP induction port (USP throat). An aliquot (10 mL) of solvent mixture of methanol:water:0.2 M HCl (7:2:1, v/v) was placed into each impinger stage before experiment. A relatively lower volume of collection solvent than the standard volume of 20 mL was applied so as to generate sufficient drug concentrations for HPLC analysis, which should not affect dispersion patterns. A glass microfiber filter (0.2 μm) was placed at the bottom of the impinger base. Each powder was weighed (approximately 10 mg) and loaded individually into a Size 3 hydroxypropyl methylcellulose capsule (Qualicaps, Whitsett, NC, USA). The power was dispersed through a RS 01 inhaler device (with a similar design to Osmohaler, Plastiape S.p.A., Osnago, Italy) at an air flow rate of 100 L/min for 2.4 s with a pressure drop of approximately 4 kP. The amount of drug deposited on the throat, four stages of the impinger, and the filter, as well as the amount retained in the device and capsules was analyzed using the HPLC method described above. The cutoff diameters for Stages 1-4 of the liquid impinger at 100 L/min were 10.4, 4.9, 2.4, and 1.2 μm, respectively. The percentage of the total dose collected on the stage 3, stage 4 and on the filter over the recovered dose, was considered as the fine particle fraction (FPF). The emitted dose (ED) was determined as the drug released from the capsule and device over the recovered dose.

Cytotoxicity Study

The A549 epithelial alveolar cells were purchased from American Type Culture Collection (ATCC) (Manassas, VA, USA). The cells were cultured in F-12K medium supplemented with 10% (v/v) heat-inactivated FBS, 100 IU/mL penicillin, and 100 μg/mL streptomycin (ATCC recommended) at 37° C. in a 5% $CO_2$ and 95% humidity atmosphere (Fisherbrand Isotemp $CO_2$ Incubator). The cell viability of free drugs, blank liposomes and drug-loaded liposomes were evaluated by the standard MTT assay (Katsumiti A, et al., *Toxicol. In Vitro.* 2018, 48, 146-158). The cells were seeded in a 96-well plate at a density of $1\times10^4$ cells per well and cultured for 24 hrs. Then, the free drugs (ciprofloxacin/colistin, 8 mg/2 mg in 1 mL) dissolved in 5% mannitol solution, blank liposome and drug-loaded liposome were diluted with culture medium to obtain a series of drug solutions, e.g. 20/5, 10/2.5, 5/1.25 and 0.25/0.0625 μg/mL (ciprofloxacin/colistin). The culture medium was replaced with these drug solutions and the cells were incubated for 24 hrs. At the end of incubation, the culture medium containing drugs was aspirated and the 96-well plate was added serum free medium and MTT solution (5 mg/mL dissolved in PBS), followed by incubation of 4 hrs. At the end of the incubation, the medium was removed, the formazan crystals were dissolved by the addition of DMSO and the absorbance was measured at 570 nm using a microplate absorbance reader (BioTek, Bio Tek Instruments, Inc., Winooski, VT, USA).

Minimum Inhibitory Concentration

MICs of colistin and ciprofloxacin solutions against *P. aeruginosa* H131300444 and *P. aeruginosa* H133880624 were determined by a broth microdilution method, which is normally applied as a reference method for isolates to be tested by killing curve assays. Briefly, fresh cultures of each strain were diluted in Cation-Adjusted Mueller-Hinton Broth (CAMHB; $Mg^{2+}$ at 12.2 mg/L and $Ca^{2+}$ at 23.0 mg/L [Oxoid, Hampshire, England]) giving an approximately inoculum of $10^{\wedge 6}$ colony-forming units (CFU/ml) as the inocula. Drug concentrations of 0, 0.125, 0.25, 0.5, 1, 2, and 4 mg/L were derived from diluting the stock drug solution (5.12 mg/mL) with CAMHB. After 20 hrs incubation at 35° C., the presence or absence of growth was observed for each microplate. The MIC was defined as the lowest concentration of antibiotic that completely inhibited the growth of the organism.

In Vitro Static Time-Kill Experiment

Static time-kill studies were conducted for colistin, ciprofloxacin and reconstituted USFD liposomal powder (colistin: ciprofloxacin=2 mg/mL:8 mg/L) against clinical isolates of multidrug resistant *P. aeruginosa* H131300444 and *P. aeruginosa* H133880624. All samples were dissolved in CAMHB and all experiments were performed with an initial inoculum of ~$10^6$ CFU/mL in 20 mL of CAMHB in 50 mL pyrogen-free and sterile polypropylene tubes. Based on our preliminary data, drug concentrations of 2 mg/L and 8 mg/L were tested for both solutions and USFD liposomal powder. As for the USFD liposomal powder, drug concentrations were made by rehydrating the liposomal powder with double distilled water and then diluting the liposomal formulation with the broth to achieve the target drug concentration (colistin:ciprofloxacin=2 mg/mL:8 mg/L). Serial samples (50 μL) were obtained at 0, 1, 3, 6 and 24 hrs for viable cell counting and determination of drug concentrations. All samples were centrifuged at 12000×g for 10 min and cell pellets were resuspended in 0.9% saline and diluted accordingly for viable counting on nutrient agar plates. The bacteria were incubated at 37° C. for 24 hrs and the limit of detection was 20 CFU/mL (equivalent to one colony per plate). The colonies were counted with a ProtoCOL colony counter (Synbiosis, Cambridge, United Kingdom).

Characterization of Cipro-Col-Lips Powders

The composition of cryoprotectants in different formulations were shown in the Table 6. The size, PDI and zeta potential of Cipro-Col-Lips powders after rehydration were shown in Table 7. The kinds and concentrations of cryoprotectants all had an effect on the size. Although different cryoprotectants had significant effect on the size ($P<0.05$), the PDIs were all under 0.3, which implied that all formulations had a monodisperse distribution. The F8 including 8% mannitol, 2% sucrose and 5% PVP 10 had the smallest size.

TABLE 5

The composition of cryoprotectants in different formulations.

| Formula* | Hydrated solution | Added cryoprotectants before USFD |
|---|---|---|
| F1 | 8% Man + 2% Suc + 0.5 mol/L AS | 1% Leu + 1% PVP 10 |
| F2 | | 1% Leu |
| F3 | | 2% F68 |
| F4 | | 5% F68 |
| F5 | | 2% F127 |
| F6 | | 5% F127 |
| F7 | | 1% PVP 10 |
| F8 | | 5% PVP 10 |
| F9 | | 1% PVP K30 |
| F10 | | 5% PVP K30 |
| F11 | | 1% PVP K90 |
| F12 | | — |

*The volume of formulations was diluted two-fold before USFD. Suc means sucrose, Man means mannitol, Leu means leucine and AS means ammonium sulfate.

The morphologies of the Cipro-Col-Lips dry powders prepared by USFD method were visualized via scanning electron microscopy. Morphologies had no significant different for the USFD particles with different cryoprotectants. All the particles showed a near-spherical shape and more porous structure.

TABLE 6

Rehydration characteristics of Cipro-Col-Lips powders (mean ± SD, n = 3).

| Formula | Size (nm) | PDI | Zeta potential (mV) |
|---|---|---|---|
| F1 | 391.1 ± 9.9 | 0.198 ± 0.042 | −16.5 ± −0.4 |
| F2 | 428.4 ± 20.9 | 0.294 ± 0.064 | −23.2 ± −1.0 |
| F3 | 246.8 ± 5.1 | 0.243 ± 0.017 | −18.6 ± −0.4 |
| F4 | 228.4 ± 7.3 | 0.222 ± 0.042 | −19.4 ± −0.8 |
| F5 | 255.9 ± 1.0 | 0.275 ± 0.068 | −20.4 ± −0.7 |
| F6 | 215.1 ± 8.3 | 0.238 ± 0.018 | −21.0 ± −0.6 |
| F7 | 183.3 ± 4.2 | 0.254 ± 0.055 | −20.9 ± −0.7 |
| F8 | 153.8 ± 2.3 | 0.185 ± 0.022 | −11.4 ± −0.4 |
| F9 | 223.7 ± 6.1 | 0.216 ± 0.004 | −21.3 ± −1.0 |
| F10 | 191.6 ± 2.3 | 0.239 ± 0.037 | −9.2 ± −0.4 |
| F11 | 271.3 ± 2.1 | 0.232 ± 0.022 | −20.8 ± −0.8 |
| F12 | 378.9 ± 8.5 | 0.256 ± 0.077 | −12.4 ± −0.7 |

Optimization of the USFD Powder Formulations

Ultrasonic spray freeze drying (USFD) is one of the methods which can produce large porous particles by using the process of ultrasonic atomization, rapid freezing, and lyophilization. Saccharides such as sucrose, mannitol and trehalose are usually used as cryoprotectants to stabilize liposome particles during the freeze-drying process. However, most of these sugars being amorphous will add to moisture absorption of liposome dry powders, and seriously impacted the stability of DPIs for the pulmonary administration. Therefore, it is of a great importance to inhibit the crystallization of amorphous sugar as to improve the stability of the liposomal formulations. It has been proved that polymer such as polyvinylpyrrolidone (PVP) and poloxamer could inhibit nanoparticle aggregation, thus preserve particle size distribution and mean nanoparticles size. All sugar cryoprotectants were used at a total concentration of 10% (mannitol 8% and sucrose 2%, w/v). The selected concentrations of poloxamer 188 and poloxamer 407 were 2% and 5% (w/v), and the ratios of PVP 10 and PVP K30 were 1% and 5% (w/v), respectively. The content of PVP K90 was 1% (w/v). Cipro-Col-Lips dry powders were reconstituted by Milli-Q water to form liposomal suspensions. The encapsulation efficiency (EE) and fine particle fraction (FPF) were obtained to evaluate the protection capability of the cryoprotectants.

Significant difference ($P<0.05$) was found in the EE and the drug deposition in each stage between different Cipro-Col-Lips formulations. The EE of F8, containing 8% mannitol, 2% sucrose and 5% PVP 10, was the highest than other formulations. The liposomes with 8% mannitol, 2% sucrose and 5% PVP 10 had the smallest particle size, the most uniform distribution and the highest EE %, which implied that 8% mannitol, 2% sucrose and 5% PVP 10 as the cryoprotectants have the best lyophilization protection ability during USFD compared with other formulations. However, the Cipro-Col-Lips dry powder (F1), containing 8% mannitol, 2% sucrose, 1% leucine and 1% PVP 10, had the highest FPF, which implied that F1 had a uniform and higher drug deposition from Stage 3 to Stage 8 compared to other formulations. All Cipro-Col-Lips dry powder inhaler formulations with different cryoprotectants had high ED>90% with no significant difference among the formulations ($P>0.05$).

In the course of the present experiments, polyvinylpyrrolidone, type PVP 10 was found superior to poloxamer or leucine in preserving the EE of liposomes. Combining the results of FPF, Cipro-Col-Lips powder with 8% mannitol and 2% sucrose (w/v, as the internal cryoprotectant), and 8% mannitol, 2% sucrose and 1% PVP 10 (w/v, as the external cryoprotectants), having the ideal characteristics were selected for the further investigation.

Powder X-Ray Analysis

X-ray diffractograms of the drugs, excipients and USFD liposomes powders are performed. The diffractograms of colistin, PVP 10, PVP K30 and PVP K90 colistin showed that they were in the amorphous form with none of the diffraction peaks. Sharp peaks were observed for the USFD liposome formulations, ciprofloxacin, mannitol and sucrose. However, PXRD patterns of USFD liposome powders were almost consistent with the pattern of USFD mannitol.

Statistical Analysis

All the tests were carried out as least in triplicate and the results were reported as the mean values with standard deviation. Statistical differences in FPF and ED were analyzed by one-way analysis of variance (ANOVA). Probability values of less than 0.05 were considered as a statistically significant difference.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected. It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

What is claimed is:

1. A pharmaceutical composition comprising a polymyxin compound and a quinolone compound, or a pharmaceutically acceptable salt thereof, respectively, a phosphatidylcholine (PC), an anionic lipid and cholesterol, wherein polymyxin and quinolone, or a pharmaceutically acceptable salt thereof, respectively, are encapsulated into or on a liposome formed by said PC, anionic liquid and cholesterol, and wherein said PC and said anionic lipid are in a ratio of about 1:20 to about 20:1 mol/mol, and the polymyxin to quinolone compound ratio is from about 1:10 to about 10:1 mol/mol.

2. A method for treating a subject with an infection by a bacterium comprising the step of administrating a pharmaceutical composition according to claim 1 to said subject in need thereof.

3. The method of claim 2, wherein the subject is infected with *Pseudomonas aeruginosa*.

4. The method of claim 3, wherein the *P. aeruginosa* is resistant to treatment with monotherapy with colistin or ciprofloxacin.

5. The pharmaceutical composition of claim 1, wherein said polymyxin is colistin, polymyxin B or a pharmaceutically acceptable salt thereof; and said quinolone is ciprofloxacin, levofloxacin, moxifloxacin, gemifloxacin, gatifloxacin, garenoxacin, or a pharmaceutically acceptable salt thereof.

6. The pharmaceutical composition of claim 1, wherein said phosphatidylcholine (PC) is soybean phosphatidylcholine (SPC), egg phosphatidylcholine (EPC), hydrogenated soybean phosphoatidylcholine (HSPC), 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), or 1,2-dioleoyl-sn-glycero-3-phosphocholine (DOPC).

7. The pharmaceutical composition of claim 1, wherein said anionic lipid is a phosphoglycerol (PG) selected from the group consisting of 1,2-distearoyl-sn-glycero-3-phosphoglycerol (DSPG), 1,2-dimyristoyl-sn-glycero-3-phosphoglycerol (DMPG), and 1,2-dipalmitoyl-sn-glycero-3-phosphoglycerol (DPPG); or a phosphatidic acid (PA) selected from the group consisting of 1,2-dimyristoyl-sn-glycero-3-phosphatidic acid (DMPA), 1-2-dipalmitoyl-sn-glycero-phosphatidic acid (DPPA), and 1,2-dimyristoyl-sn-glycerol-3-phosphatidic acid (DSPA).

8. The pharmaceutical composition according to claim 7, wherein said PG is a salt and said PA is a salt.

9. The pharmaceutical composition according to claim 1, wherein said liposome is manufactured by an active drug loading method, or wherein said liposome is manufactured by a passive drug loading method.

10. The pharmaceutical composition of claim 1, wherein said pharmaceutical composition is freeze-dried or spray freeze-dried.

* * * * *